United States Patent [19]

Tajima et al.

[11] Patent Number: 5,855,553
[45] Date of Patent: Jan. 5, 1999

[54] REMOTE SURGERY SUPPORT SYSTEM AND METHOD THEREOF

[75] Inventors: Fujio Tajima, Ibaraki-ken; Masakatsu Fujie, Ushiku; Isao Nakajima, Baraki-ken; Hiroshi Takeuchi, Matsudo; Toshihiko Wada, Tokyo, all of Japan

[73] Assignee: Hitchi, Ltd., Tokyo, Japan

[21] Appl. No.: 601,356

[22] Filed: Feb. 16, 1996

[30] Foreign Application Priority Data

Feb. 16, 1995 [JP] Japan ................................ 7-28391

[51] Int. Cl.[6] .................................................. A61B 5/00
[52] U.S. Cl. ......................... 600/407; 600/427; 600/429; 600/474; 600/476; 606/1; 606/16; 606/130; 607/1; 395/82; 395/83; 395/99
[58] Field of Search ............................. 128/653.1, 653.2; 601/2–4; 606/1, 14, 2, 13, 130, 15, 16; 607/1, 88, 96; 395/80–84, 99; 600/407, 410, 425, 411, 427, 429

[56] References Cited

U.S. PATENT DOCUMENTS

| 4,545,713 | 10/1985 | Beni et al. ................................ 606/19 |
| 5,078,140 | 1/1992 | Kwoh ................................... 128/653.1 |

FOREIGN PATENT DOCUMENTS

| 3121064 | 5/1991 | Japan . |
| 0453533 | 2/1992 | Japan ................................... 128/653.2 |
| 4146097 | 5/1992 | Japan . |

OTHER PUBLICATIONS

Symposium on Robotics Mechatoronics in 1993, The Japan Society of Mechanical Engineers.

*Primary Examiner*—Ruth S. Smith
*Attorney, Agent, or Firm*—Antonelli, Terry, Stout & Kraus, LLP

[57] ABSTRACT

A remote surgery supporting system and a method thereof produces a presentation of realism control data generated by realism control data generating means 101 from image data obtained from work environment data detecting means 104 and measurement data processing means 118 and from force and proximity data. While viewing this presentation, the surgical operator inputs actions through action command inputting means 114 and thereafter, diseased tissue manipulating means 102 executes a procedure on diseased part 125. The manipulation force of each surgical operator received from manipulation command generating means 103 and force reflection from the diseased part 125 are combined and presented to the action command inputting means 114. Thereby, a plurality of surgical operators can perform a surgerical operation while viewing the realism control data and sensing the manipulation force of other surgical operators and the force reflection from the diseased part. Thus, a master/slave type remote surgery supporting system which allows a plurality of surgical operators to perform a surgical operation which requires many degrees of freedom can be provided.

40 Claims, 31 Drawing Sheets

FINE MOTION PART

REMOTE SURGERY SUPPORT SYSTEM AND METHOD THEREOF

BACKGROUND OF THE INVENTION

The present invention relates to a remote surgery supporting system and a method thereof, and more particularly, it relates to a remote surgery supporting system and a method which is suitable for supporting one or more surgical operators in performing a surgical treatment on the brain, nervous system, eyeballs or the like by remote-controlling surgical tools or therapeutic instruments using a manipulator having a high degree of freedom.

Hitherto, as a system for performing an operation on the cranial nerve or the like while observing data of measuring instruments which are visually reconstructed, there has been known a magnetic resonance monitoring treatment system by which the position of a catheter is automatically controlled by a positioning mechanism when a surgical operator inputs a position and instructs of the catheter while observing image MRI produced by as disclosed in Japanese Patent Laid-open No. Hei. 4-53533, for example.

Further, as a system for cerebral surgical works, there has been a puncturing manipulator for stereotaxy, as disclosed in Japanese Patent Laid-open No. Hei. 3-121064, for example. As a system for performing surgery by way of remote control, there has been a system having a remote-controlled surgical manipulator in a double-piped probe, as disclosed in Japanese Patent Laid-open No. Hei. 4-1146097, for example.

Further, there has been known a micro-handling system constructed so as to allocate degrees of freedom to turning and translation to a manipulator and a stage as disclosed in a collection of papers pp. 693–696 of the Symposium on Robotics Mechatoronics in 1993, The Japan Society of Mechanical Engineers.

The system described in the above-mentioned Laid-open No. Hei. 4-53533 is supposed to be used for treatment mainly by means of a catheter and it is difficult to perform with it an operation which requires a direct manipulation of a diseased part with a highly sophisticated technical skill, such as removal of a tumor adhering on a blood capillary or nerve.

Furthermore, because an ultrasonic motor (piezoelectric element) is used for an actuator to operate in a static magnetic field, it is difficult to increase the compliance to enable treating of soft tissues.

It is also incomplete more or less in terms of the mode for supporting data because the modality thereof is only magnetic resonance, so that it is hard to understand changes in a shape of a cranial bone when a craniotomy is performed, and the measured contents only show shapes and no functional measurement is implemented and the measured and displayed contents show a 2-dimensional tomographic image which is not intuitional.

The system described in the above-mentioned Patent Laid-open No. Hei. 3-121064 is used for stereotaxy and is capable of performing only puncturing. However, there are many troubles of the cranial nerve which cannot be surgically treated well only by puncturing and which require a plurality of mechanisms having a greater degree of freedom in order to manipulate tissues of a diseased part. The above-mentioned system is unable to deal with such a case. Further, the disclosure describes nothing about other parts for controlling the puncturing manipulator.

The system disclosed in the above-mentioned Patent Laid-open No. Hei. 4-146097 isolates the surgical operator completely from the patient, so that there will be difficulty in responding to an emergency and even if possible, it may be too late.

The system described in the collection of papers of the Symposium on Robotics Mechatoronics in 1993, The Japan Society of Mechanical Engineers, is constructed so that the work cannot be started unless an object is placed on the stage and is not suitable for actual surgical works.

Further, in all the examples described above, the master manipulator and the slave manipulator correspond in a relation of one-to-one to the end and no consideration is given to the enhancement of works and simplification of control attained by controlling a plurality of slave manipulators by one master manipulator and to the training function attained by controlling one slave manipulator by a plurality of master manipulators.

Still further all the known examples described above suppose tacitly that one surgical operator manipulates the system and describe nothing about a joint surgical work function performed by a plurality of surgical operators, the manipulation of one slave manipulator by a number of master manipulators, and the training function thereof.

In the known examples described above, the data has been obtained only for the use of the surgical operator at the end regardless of whether it occurs before or during the operation.

Furthermore, there is no function of giving a surgical simulation and so there could be no benefit from the result regardless whether the object of the surgery is an actual dummy vital tissue or a model in a computer.

SUMMARY OF THE INVENTION

Accordingly, it is an object of the present invention to provide a remote surgery supporting system and a method thereof for supporting one or more surgical operators in performing a surgical treatment of brain, nervous system, eyeballs or the like by remote-controlling surgical tools or therapeutic instruments using a manipulator having a high degree of freedom while seeing data of various measuring instruments which are visually reconstructed.

It is another object of the present invention to provide a master-slave type remote surgery supporting system and a method thereof which make it possible to perform surgical operations which require a large degree of freedom and cooperation at the terminal within a narrow space.

It is still another object of the present invention to provide a multi-master and multi-slave type remote surgery supporting system and a method thereof which allow a plurality of surgical operators to perform surgical operations in cooperation.

It is a further object of the present invention to provide a remote surgery supporting system and a method thereof which compensate for a drop of working skill of a surgical operator caused by a drop of eyesight and degradation of terminal resolution due to aging.

It is another object of the present invention to provide a remote surgery supporting system and a method thereof which prevent blood infection between a patient and a surgical operator.

It is another object of the present invention to provide a remote surgery supporting system and a method thereof which realize surgery having less invasion by utilizing mainly a degeneration of tissues.

It is another object of the present invention to provide a remote surgery supporting system which will allow the surgical operators to transfer their working skill among them.

It is another object of the present invention to provide a remote surgery supporting system which makes it possible to perform consistently from a surgery training to a surgery simulation, to provide informed consent for a patient utilizing results thereof, and to perform a surgical operation.

The remote surgery supporting system of the present invention for supporting surgical works of one or more surgical operators remote-controlling a surgical tool or therapeutic instrument comprises diseased tissue manipulating means composed of the surgical tools or therapeutic instruments; in vivo data measuring means for measuring in vivo data by periodically applying one or more types of energy, including a fluctuating magnetic field, an electromagnetic wave and an ultrasonic wave to a diseased part and the surrounding parts therefore of before and during the operation and by measuring a penetrated or resonated signal; measurement data processing means for generating 3-D measured data images from the in vivo data measured by the in vivo data measuring means; working environment data detecting means for taking in image data of the diseased part and for detecting an approaching state and a contact force of the diseased tissue manipulating means to the diseased part; realism control data generating means for synthesizing and processing the output of the working environment data detecting means and the output of said measurement data processing means to present each surgical operator with realism control data; action command inputting means for inputting actions taken by each surgical operator based on the realism control data presented to each surgical operator by the realism control data generating means; and manipulation command generating means for translating the action command output from the action command inputting means to manipulation command data, for transmitting it to the diseased tissue manipulating means and for transmitting the contact force detected by the working environment data detecting means to the diseased tissue manipulating means.

A mechanism for positioning the surgical tools or therapeutic instruments of the diseased tissue manipulating means of the present invention is made of a material and is constructed by a drive theory so as to be less sensitive to the magnetic field.

Further, the realism control data generated by the realism control data generating means of the present invention contains at least one of: a virtual image to be presented to the surgical operator by synthesizing the image data taken in by the working environment data detecting means and the measured data image generated by the measurement data processing means; a virtual sound field to be presented to the surgical operator as sound data; and virtual force reflection data to be presented to the surgical operator by combining it with the contact force in the manipulation command generating means.

The manipulation command generating means of the present invention transmits a synthesized force reflection, obtained by combining force sensor data detected by the working environment data detecting means and a virtual force reflection generated by the realism control data generating means, to each surgical operator via the action command inputting means.

Further, according to the present invention, the diseased tissue manipulating means is positioned against the diseased part via the surgical tool or therapeutic instrument as it receives the manipulation command as an input and causes deformation, destruction or degeneration of diseased tissues by generating or transmitting at least one type of energy, including kinetic energy, light energy, electrical energy and thermal energy.

The remote surgery supporting system of the present invention further comprises data storage means for storing one or both of the realism control data generated by the realism control data generating means and the measured data image generated by the measurement data processing means to add a function of training surgical operators by simulating the surgical works using data stored in said storage means, or a function of presenting the data stored in said storage means to explain the condition of a disease.

Further, according to the present invention, models for generating one or both of the realism control data and measured data image are stored to add a function of a training surgical operators by simulating surgical works using that model, or a function of presenting the data stored in said storage means to explain the condition of a disease.

Still more, a remote surgery supporting method of the present invention for supporting one or more surgical operators performing surgical works on a diseased part by driving a slave manipulator equipped with a surgical tool or therapeutic instrument by manipulating a master manipulator comprises a step of driving one slave manipulator in response to a combined command obtained by multiplying action commands output from the master manipulators of the surgical operators with a predetermined weighing factor and adding them.

As described above, the present invention can realize a remote surgery supporting system for supporting one or more surgical operators in performing a surgical treatment on the brain, nervous system, eyeballs or the like by remote-controlling surgical tools or therapeutic instruments using a manipulator having a high degree of freedom while observing data of various measuring instruments which are visually reconstructed.

Further, the present invention can realize a master-slave type remote surgery supporting system which makes it possible to perform surgical works which require a large degree of freedom and cooperation at the terminal within a narrow space.

Still more, the present invention can realize a remote surgery supporting system which can compensate for a drop in the working skill of a surgical operator caused by a reduction in eyesight and degradation of terminal resolution due to aging.

The present invention can also realize a remote surgery supporting system which prevents blood infection between a patient and a surgical operator.

The present invention can realize a remote surgery supporting system which can perform surgery having less invasion by utilizing mainly a degeneration of tissues.

The present invention can realize a remote surgery supporting system which allows the surgical operators to transfer their working skill among them.

The present invention can realize a remote surgery supporting system which makes it possible to perform consistently from surgery training to surgery simulation, to informed consent for a patient utilizing results thereof, and to a surgical operation.

DESCRIPTION OF PREFERRED EMBODIMENTS

Figure 1:
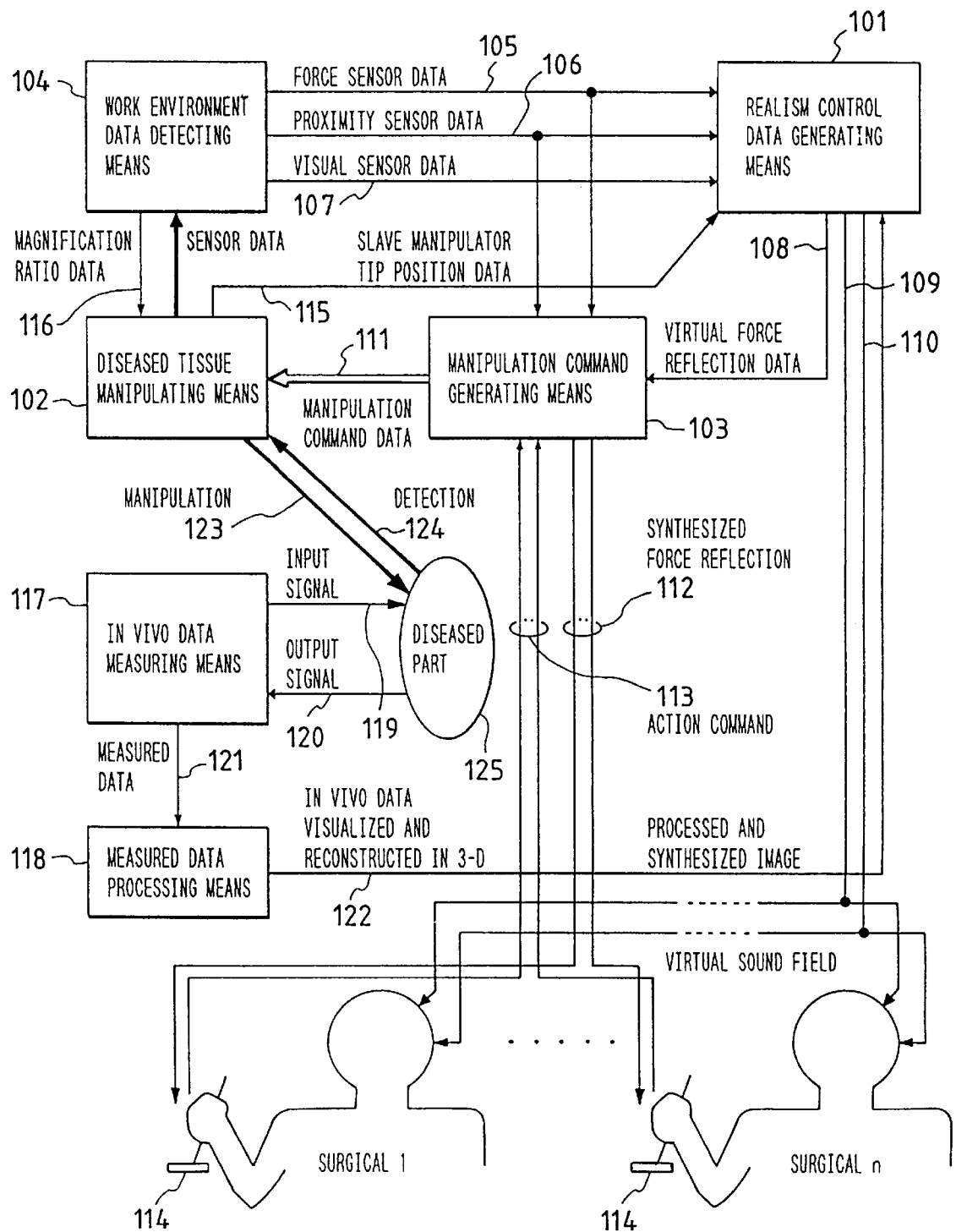
FIG. 1 is a block diagram showing one embodiment of a remote surgery supporting system of the present invention.

The present invention will be explained in detail based on preferred embodiments thereof. FIG. 1 is a block diagram showing one embodiment of a remote surgery supporting system of the present invention, which comprises realism control data generating means 101 for outputting virtual force reflection data 108, a synthesized processed image 109 and a virtual sound field; diseased tissue manipulating means 102, which is composed of a slave manipulator for outputting slave manipulator position data 115; manipulation command generating means 103 for outputting manipulation command data 111 and synthesized force reflection 112; work environment data detecting means 104 for outputting force sensor data 105, proximity sensor data 106, visual sensor data 107 and magnification ratio data 116; in vivo data measuring means 117 for outputting an input signal for measuring the inside of an organism and in measured data of the inside of the organism 121 and for receiving an output signal 120 passed through or reflected from the inside of the organism; measurement data processing means 118 for outputting visualized in vivo data 122 reconstructed in 3-D or the like; and action command inputting means 114 for outputting an action command 113.

The work environment data detecting means 104 has sensor parts at the tip of and around the slave manipulator, which is a component of the diseased tissue manipulating means 102, and detects the diseased part and the surrounding environment thereof as detection data 124 by a visual sensor, a force sensor and a proximity sensor at the end of the aforementioned manipulator.

The realism control data generating means 101 processes and synthesizes the data detected by the work environment data detecting means 104, the in vivo 3-D reconstructed image data outputted by the measurement data processing means 118 and the slave manipulator position data 115 to generate image, sound and virtual force reflection. Thereby, it shows the state of the patient to one or more surgical operators.

The data of the force sensor and the proximity sensor is transmitted also to the manipulation command generating means 103. Actual force reflection detected by the force sensor is converted into a range which allows each surgical operator to sense. The virtual force reflection generated by the realism control data generating means 101 is synthesized (combined) with the range-converted actual force reflection and the manipulation force of other surgical operators and is transmitted to each surgical operator via the action command inputting means 114.

Each surgical operator inputs an action command to the diseased tissue manipulating means 102 via the action command inputting means 114 based on the data shown by the realism control data generating means 101. The action command is translated into the manipulation command data 111 by the manipulation command generating means 103.

The diseased tissue manipulating means 102 interprets and executes the manipulation command data 111 in accordance with a parameter of the magnification ratio data 116 to manipulate (123) the diseased tissue.

At the same time, the in vivo data measuring means 117 inputs the measuring input signal 119 to a diseased part 125 periodically and receives the output signal 120 which has passed therethrough or is reflected therefrom. This signal is digitized and is sent to the measurement data processing means 118 as the measured data.

The measurement data processing means 118 operates on the measured data obtained periodically and reconstructs the result as 3-D image data.

Figure 2:
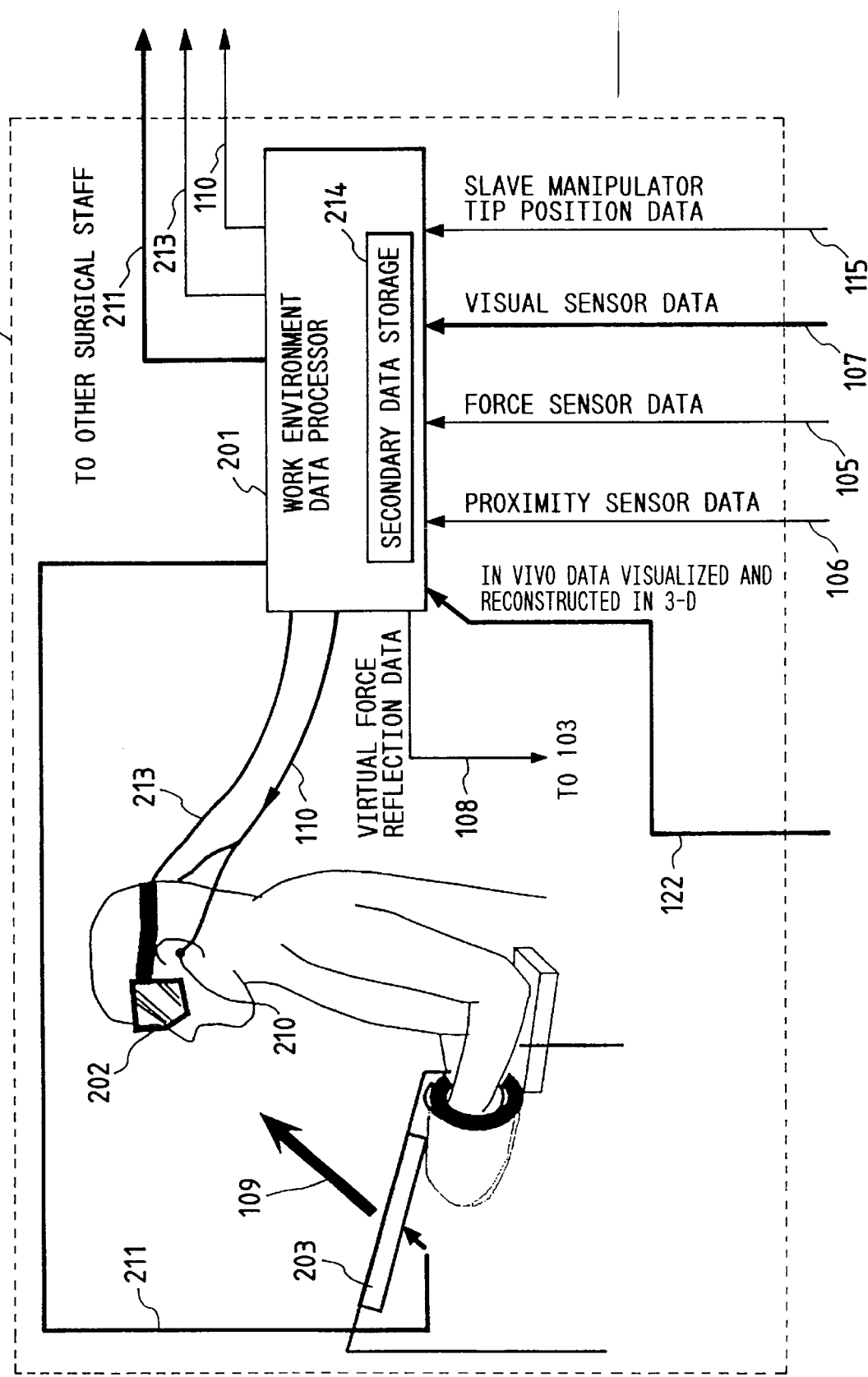
FIG. 2 is a block diagram showing one structural example of realism control data generating means.

The structure and operation of each means will be explained in detail below. FIG. 2 shows one structural example of the realism control data generating means 101. It comprises a work environment data processor 201, a binocular view field controller 202, a display 203 for displaying a processed image and virtual sound field reproducing means 210. The synthesized image data 211 is synthesized from virtual image data generated by the work environment data processor 201 and the visual sensor data 107, which produces an actual image, and is processed into and visualized with a control signal 213 of the binocular view field controller 202 and the virtual sound field 110, as output to the outside to a number of the surgical operators.

The work environment data processor 201 is equipped with a secondary data storage section 214 for recording data and is capable of recording time series data or the like of each of the visual, force and proximity sensors. This data is used for a simulation of and training for surgery as described later.

Figure 14:
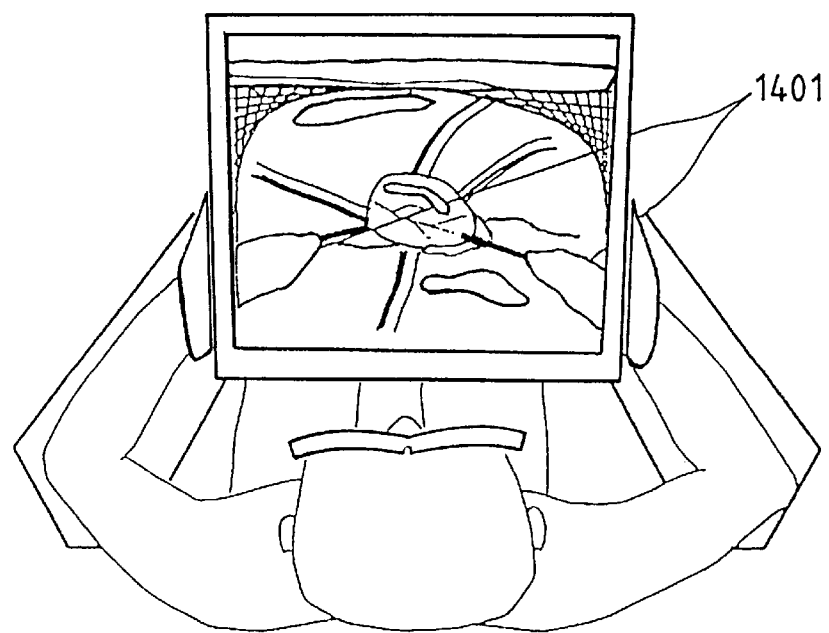
FIG. 14 is a schematic diagram showing FIG. 2 from the top.

FIG. 14 is a drawing showing FIG. 2 as seen from the top. The hands of each surgical operator beyond the wrists appear as if they are tips 1401 of the slave manipulator.

Figure 36:
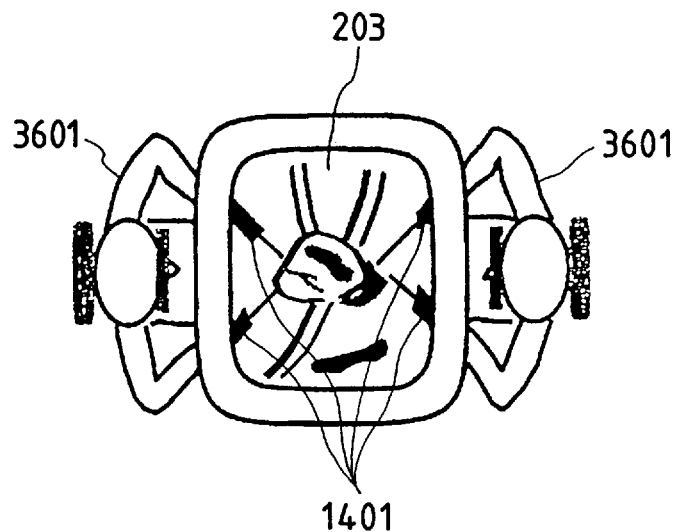
FIG. 36 is a schematic diagram showing an example in which one display is allocated to a plurality of surgical operators.
Figure 37:
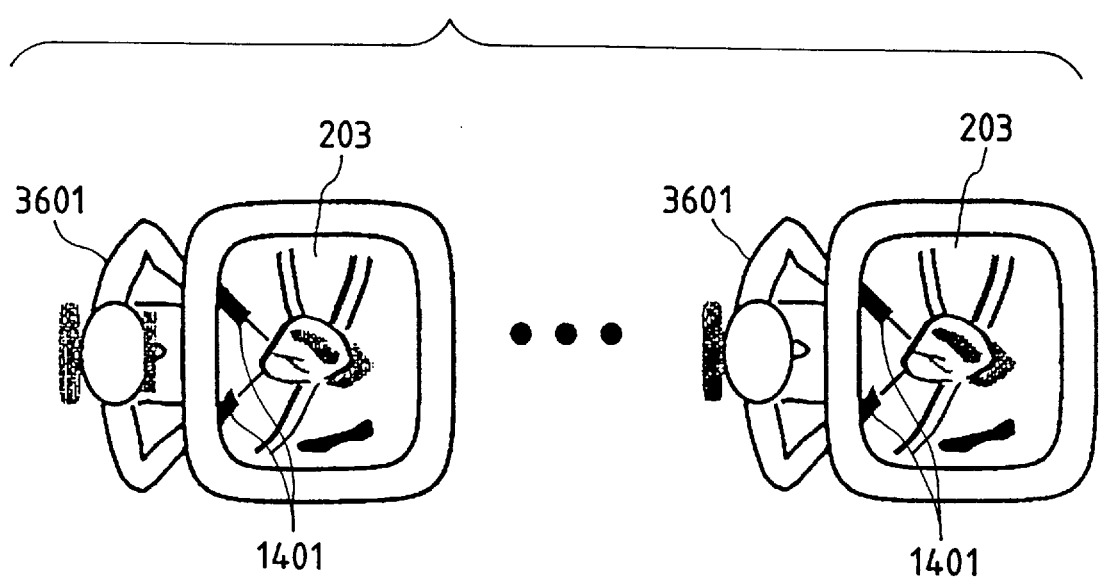
FIG. 37 is a schematic diagram showing an example in which one display is allocated to one surgical operator.

When there are a plurality of surgical operators, it is preferable to arrange the system so that one display 203 is referred to from plural directions, as shown in FIG. 36, or to arrange the system so that a respective display 203 is allocated to each surgical operator, as shown in FIG. 37.

FIG. 36 shows an arrangement for a relatively small number of surgical operators. In this case, a respective slave manipulator is allocated to each surgical operator and each surgical operator can have a feeling as if his or her own hand is extending and continuing into the display.

Further, the surgical operators can refer to the same image as if they are seeing an optically enlarged image of the diseased part (as if a lens is placed there) and can talk directly to each other.

While each surgical operator has the feeling as if his or her hand extends and continues into the display in the arrangement of FIG. 37, the actual slave manipulator is controlled by a manipulation force determined from forces of each surgical operator, which are weighed and combined. This will be described later.

In the arrangement in FIG. 37, it is not necessary to wear the binocular view field controller 202 because a seperate display is allocated to each surgical operator and it is desirable to adopt a method of realizing stereoscopy by showing different images to both eyes by using lenticular lenses for example.

An example of an operation of the work environment data processor 201 will be explained below with reference to FIGS. 15 through 24. A process for generating virtual image data will be explained first by using FIGS. 15 through 18.

Figure 15:
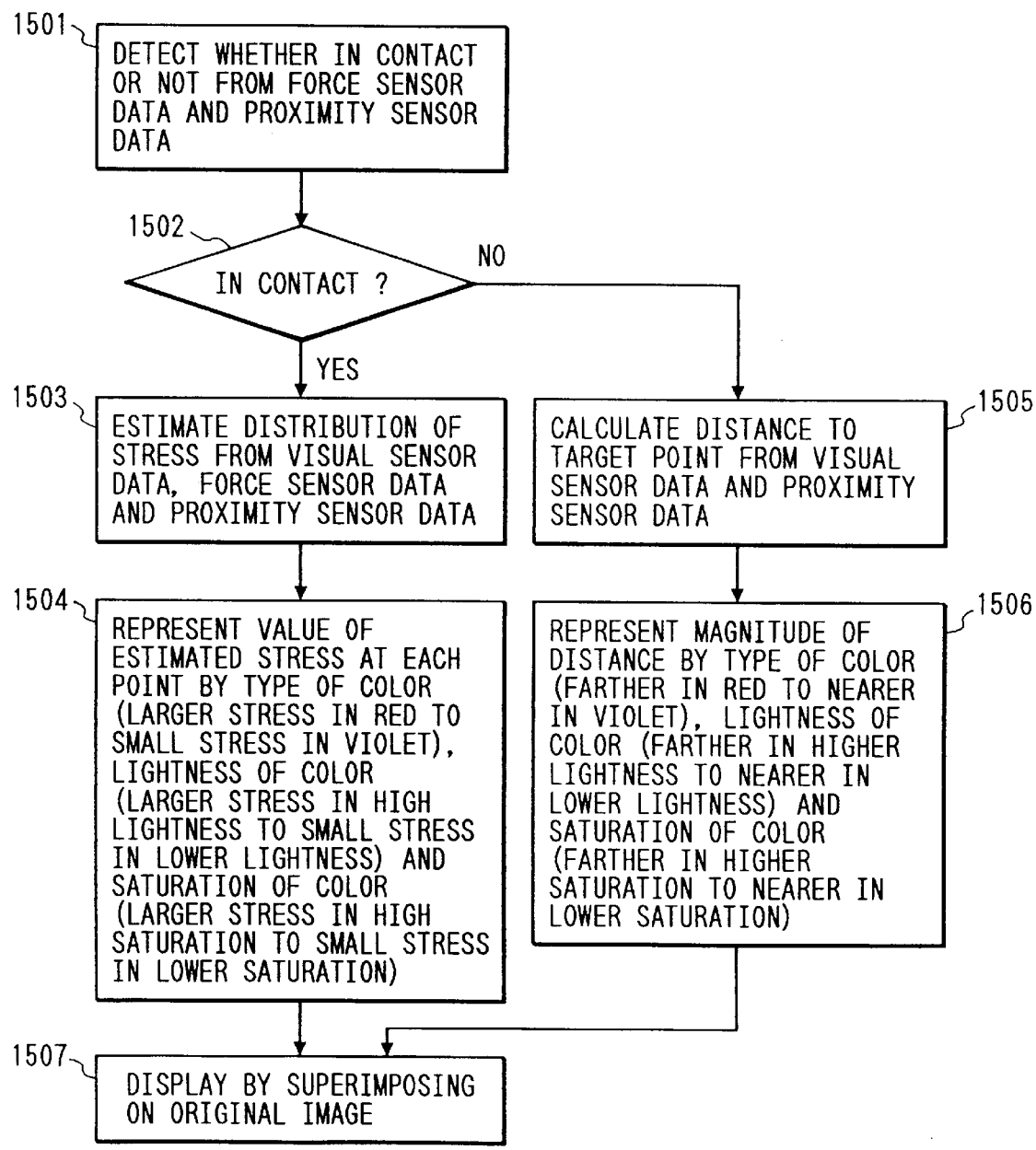
FIG. 15 is a flow chart showing an example of an algorithm for generating visualized data of a distribution of stress or distance.

In FIG. 15, it is detected and determined first whether the tip of the slave manipulator is in contact or not by examining the force sensor data 105 and the proximity sensor data 106 in Steps 1501 and 1502. When the slave manipulator is not in contact, the distance from a target position of the tip of the slave manipulator is calculated based on the visual sensor data 107 and the proximity sensor data 106 in Step 1505 and the degree of the distance is represented by using one or a plurality of characteristics, including color (e.g., farther in red to nearer in violet), lightness of color (e.g., farther in higher lightness to nearer in lower lightness) and saturation of color (e.g., farther in higher saturation to nearer in lower saturation) in Step 1506.

Here, the proximity sensor is adapted to obtain the distance data by measuring the intensity of a reflected ultrasonic or light wave and a reflection time thereof for example.

When the slave manipulator is in contact, the distribution of stress at the diseased part is estimated based on the visual sensor data 107 and the proximity sensor data 106 in Step 1503 and the magnitude of the stress at each point of the image is represented by characteristics, including color (e.g., larger stress in red to small stress in violet), lightness of color (e.g., larger stress in high lightness to small stress in lower lightness) and saturation of color (e.g., larger stress in high saturation to small stress in lower saturation) in Step 1504.

When the process in Step 1504 or Step 1506 ends, a virtual image composed of a color or the like representative of the distance or the stress is displayed by superimposing the color on the original image in Step 1507. That is, the spot where the distance between the diseased part and the slave manipulator is shorter or where more stress is applied is displayed more vividly or is colored with a specific color.

The above-mentioned image may be displayed by superimposing it on the in vivo data 122 reconstructed in 3-D or without superimposing it. In that case, it is possible to prepare different displays or to display them by opening different windows on the same display.

By the way, it is necessary to indicate whether the type, lightness and saturation of the color are representative of the distance or the stress when they are displayed in superimposition. To that end, it is preferable to arrange it so that they can be distinguished by a displayed color of the manipulator itself for example.

Figure 16:
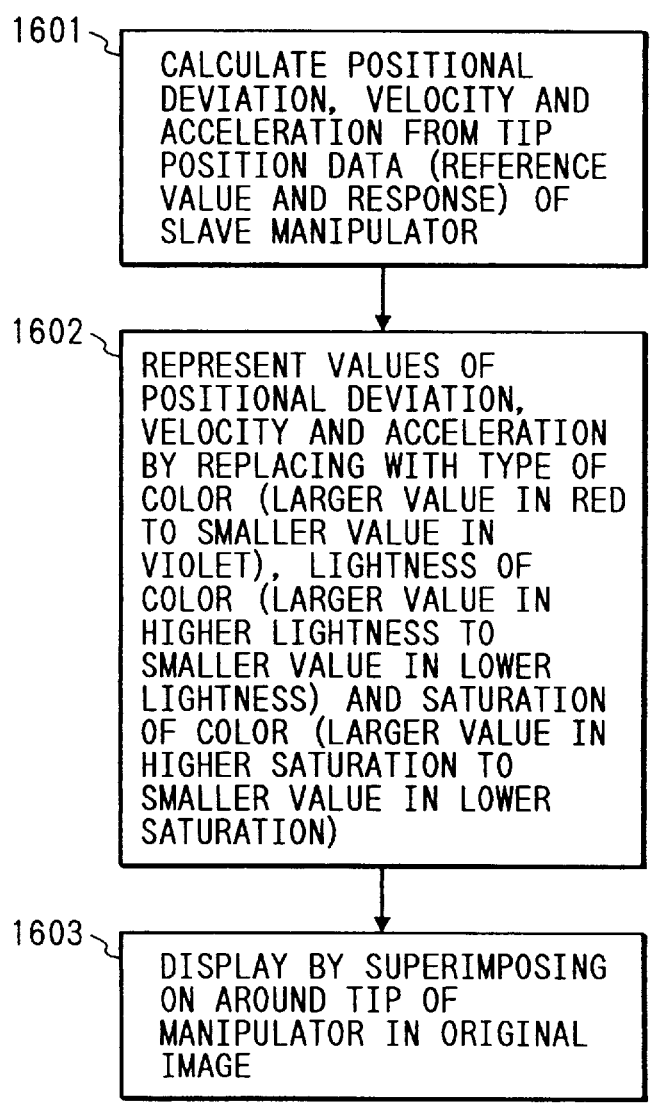
FIG. 16 is a flow chart showing an example of an algorithm for translating motion of a manipulator into color data.

FIG. 16 shows a case when a motion of the tip of the slave manipulator is displayed in correspondence with the type, lightness and saturation of color. At first, a positional deviation, velocity and acceleration of the slave manipulator are calculated from the tip position data 115 thereof which contains reference values and responses in Step 1601.

Next, the values of the positional deviation, velocity and acceleration are represented by the type of color (e.g., larger value in red to smaller value in violet), the lightness of color (e.g., larger value in higher lightness to smaller value in lower lightness) and the saturation of color (e.g., larger value in higher saturation and smaller value in lower saturation) in Step 1602. At this time, the correspondence between the positional deviation, velocity and acceleration and the type, lightness and saturation of color is arbitrary and a number of ways to indicate this is conceivable.

Finally, the representative colors are displayed around the tip of the manipulator in the original image while being superimposed thereon in Step 1603. It may be displayed by superimposing the colors on the in vivo data 122 reconstructed in 3-D or without superimposing it.

Figure 17:
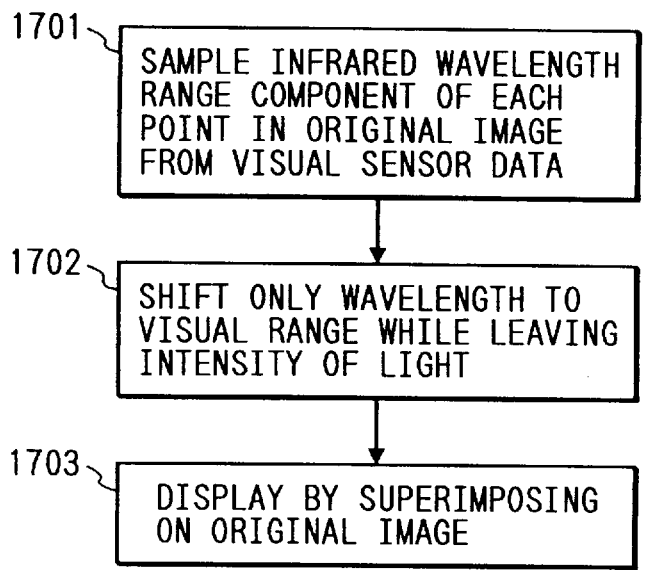
FIG. 17 is a flow chart showing an example of an algorithm for translating the motion of the manipulator into graphic data.

FIG. 17 shows a case wherein an image in an infrared wavelength range which has been converted an image that in a visual light range is displayed. At first, an infrared component at each point within the original image is sampled from the visual sensor data 107 in Step 1701. Next, only the wavelength of the infrared component of each point is shifted to a visual range while leaving the intensity of light of the component as it is in Step 1702. Finally, the image is displayed by superimposing it on the original image in Step 1703. Thereby, the displaying method described above allows the diseased position to be readily specified by visualizing a distribution of temperature which is originally invisible because the temperature of the ill part of the tissue is often different from that of the surrounding part in general.

It is also possible to use the in vivo data reconstructed in the image, such as image data given by an MRI, X-ray CT and ultrasonic CT.

It may be also preferable to display the image by superimposing arrows and effect lines on the image for making the motion of the slave manipulator within the environment comprehensible and including letters of onomatopoeic words and mimetic words for explaining the situation.

Figure 18:
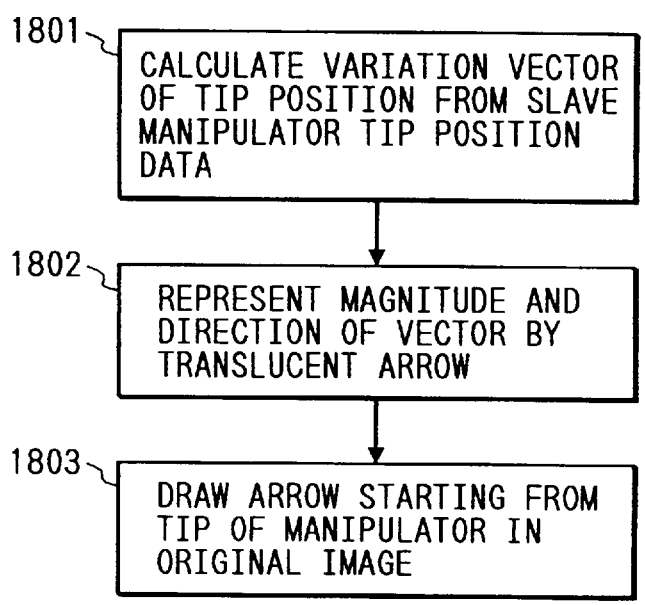
FIG. 18 is a flow chart showing an example of an algorithm for generating visualized data of a distribution of temperature of a diseased part.

FIG. 18 shows one example thereof. At first, a time derivative of a position vector of the tip or a variation vector between sampled times is calculated from the position data 115 in Step 1801. Then, the magnitude and direction of the vector are indicated by a translucent arrow in Step 1802 and the arrow is drawn starting from the tip of the manipulator in the original image in Step 1803.

The virtual image data generated or synthesized by the process in FIGS. 15 through 18 as described above is presented as a stereoscopic image to the operator (surgical operator) by driving the binocular view field controlling means 202 and the display 203 for displaying the synthesized image in synchronism.

As shown in FIG. 36, in the case wherein one display 203 is referred from multiple directions, we could adopt either a way wherein left and right eyesight are obstructed in turn and the images for the left and right eye are displayed in synchronism, or a way wherein two images with slight parallax are displayed by dividing a display into two, which are seen through some kind of special lens.

When the display is allocated to each surgical operator as shown in FIG. 37, it is possible to realize a stereoscopic system which requires no device to be worn, such as the lenticular lens system described above.

The in vivo data 122 reconstructed in 3-D may be also superimposed on the above-mentioned image. In that case, the image may be displayed by providing another display or by opening another window on the same display.

As described above, the algorithms shown in FIGS. 15 through 18 allow for more reality to be added to the actual image and the operability of each surgical operator to be increased.

Further, a decision higher in grade than that in the past can be made by referring to the in vivo data image and the actual image at the same time.

Still more, because it becomes possible to accurately catch the position of the diseased part, an accurate surgical operation can be performed on a morbid tissue which is hardly visible.

Figure 19:
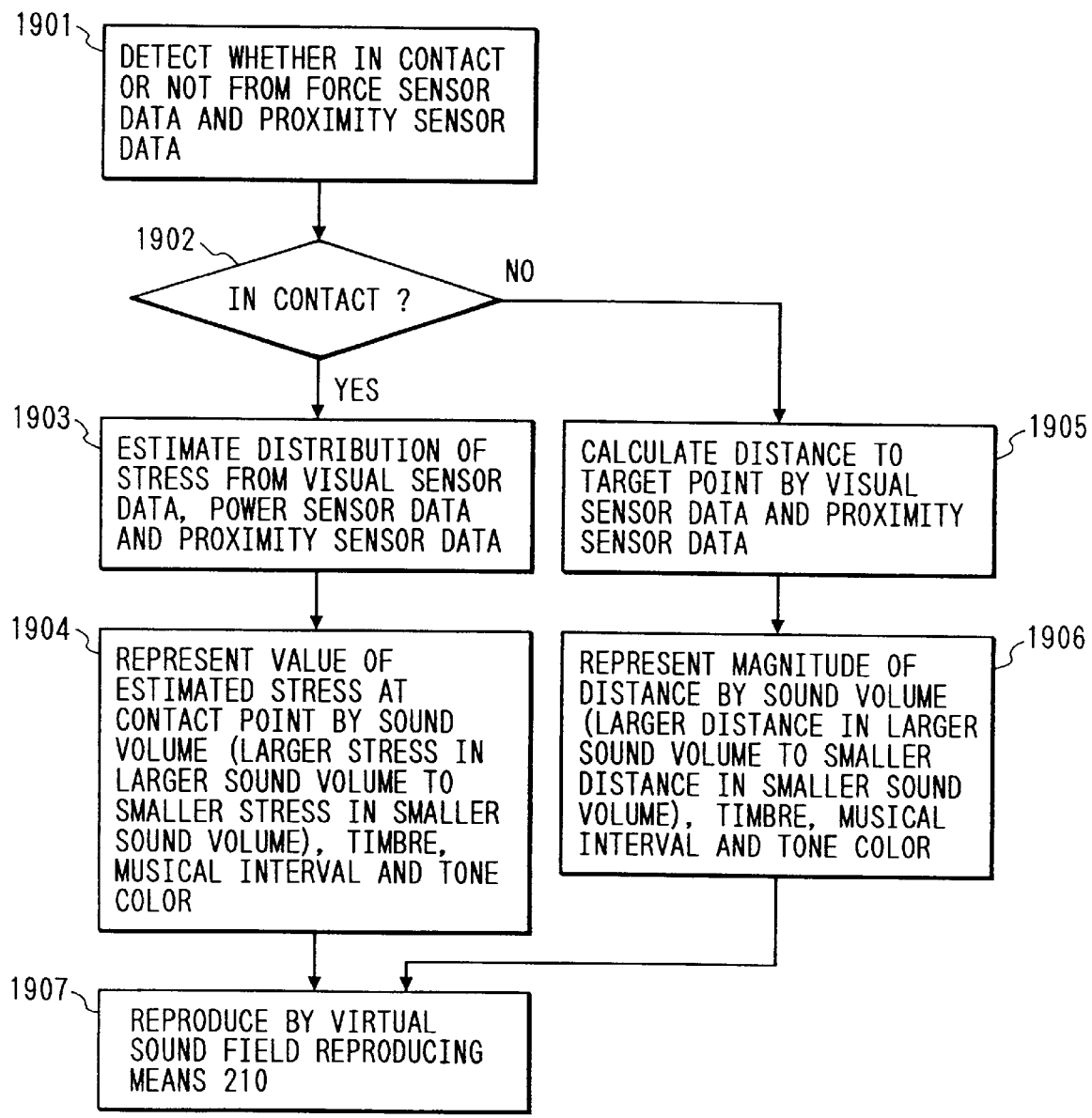
FIG. 19 is a flow chart showing an example of an algorithm for generating audible data of the distribution of stress or the distance.

The process for generating the virtual sound field 110 using the work environment data processor 201 will be explained below with reference to FIGS. 19 through 22. In FIG. 19, it is detected and determined first whether the tip of the slave manipulator is in contact or not from the force sensor data 105 and the proximity sensor data 106 in Steps 1901 and 1902.

When the slave manipulator is not in contact, the distance is calculated based on the visual sensor data 107 and the proximity sensor data 106 in Step 1905 and the magnitude of the distance is represented by one or a plurality of characteristics, including sound volume (e.g., farther in larger sound volume to nearer in smaller sound volume), timbre (time change of sound volume) (e.g., farther in larger change to nearer in smaller change), musical interval (height of sound) (e.g., farther in higher musical interval to nearer in lower musical interval) and tone color (distribution of components of fundamental wave and higher harmonic) (e.g., farther in fewer components to nearer in more components) in Step 1906.

When the slave manipulator is in contact with the diseased part, a distribution of stress at the diseased part is estimated based on the visual sensor data 107 and the proximity sensor data 106 in Step 1903 and the magnitude of the stress at one point of the tissue closest to the tip of the manipulator is represented by using one or a plurality of characteristics, including the sound volume (e.g., larger stress in larger sound volume to smaller stress in smaller sound volume), timbre (time change of sound volume) (e.g., larger stress in larger change to smaller stress in smaller change), musical interval (height of sound) (e.g., larger stress in higher musical interval to smaller stress in lower musical interval) and tone color (distribution of components of fundamental wave and higher harmonic) (e.g., larger stress in fewer components to smaller stress in more components) in Step 1904.

When the process in Step 1904 or 1906 ends, the above-mentioned sound data is reproduced by means of the virtual sound field reproducing means 210 in Step 1907. That is, the sound volume becomes larger, the musical interval becomes higher, the timbre becomes brighter or the sound type becomes metallic at the spot where the distance between the diseased part and the slave manipulator is shorter or where more stress is applied. By the way, while it is necessary to be able to distinguish whether the virtual sound field represents the distribution of stress or the distance, it can be done easily by changing the musical interval or by interrupting the sound for example.

Figure 20:
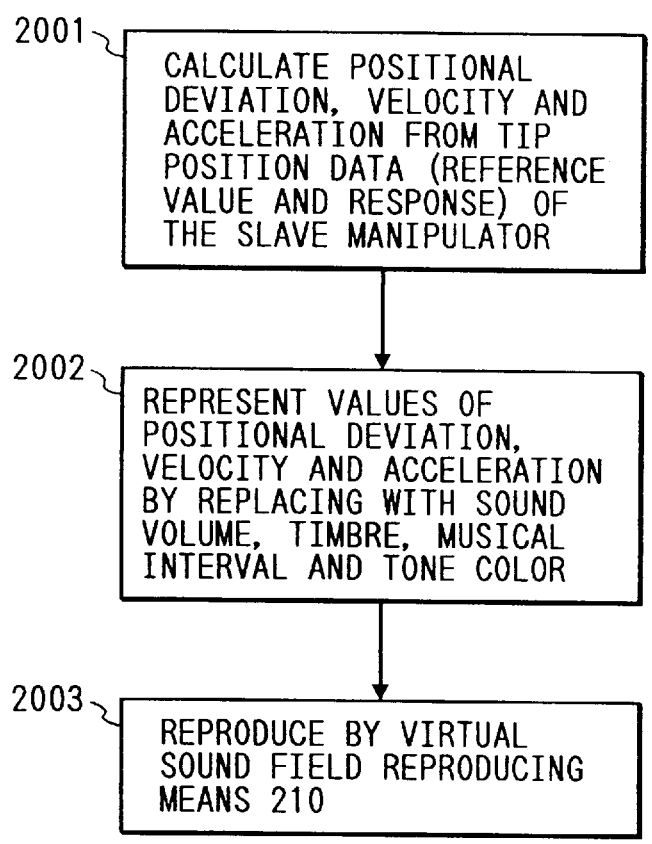
FIG. 20 is a flow chart showing an example of an algorithm for translating the motion of the manipulator into sound field data.

FIG. 20 shows a process wherein the motion of the tip of the slave manipulator is represented in correspondence with the sound volume, timbre, musical interval and tone color. At first, a positional deviation, velocity and acceleration of the slave manipulator is calculated from the tip position data 115 thereof, which contains reference values and responses, in Step 2001.

Next, the values of the positional deviation, velocity and acceleration are represented by the sound volume (e.g., larger value in larger volume to smaller value in smaller volume), the timbre (time change of sound volume) (e.g., larger value in larger change to smaller value in smaller change), musical interval (height of sound) (e.g., larger value in higher musical interval to smaller value in lower musical interval) and tone color (distribution of components of fundamental wave and higher harmonic) (e.g., larger value in fewer components to smaller value in more components) in Step 2002. At this time, the correspondence between the positional deviation, velocity and acceleration and the sound volume, timbre, musical interval and tone color is arbitrary and a number of ways effecting this is conceivable.

Finally, the representative sound is reproduced by the virtual sound field reproducing means 210 in Step 2003.

Figure 21:
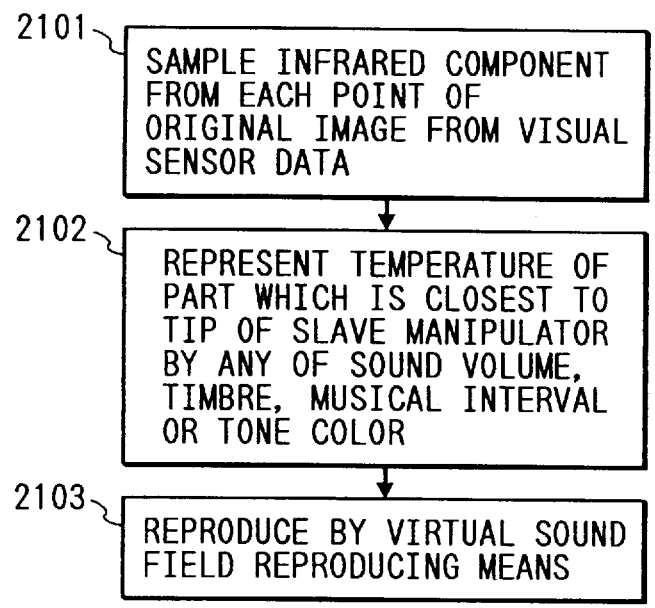
FIG. 21 is a flow chart showing an example of an algorithm for generating audible data of the distribution of temperature of the diseased part.

FIG. 21 shows a process for making a distribution of temperature obtained from an image in an infrared wavelength range to correspond with changes of sound. At first, an infrared component at each point within the original image is sampled from the visual sensor data 107 in Step 2101. Next, the intensity of light at the point closest to the slave manipulator is interpreted as a temperature and is made to correspond with any one of the sound volume, timbre, musical interval or tone color in Step 2102. Finally, it is reproduced by the virtual sound field reproducing means 210 in Step 2103.

This allows the diseased position to be readily specified by making the distribution of temperature, which is originally invisible, audible because the temperature of an ill part of the tissue is often different from that of the surrounding part in general.

It is also considered to be effective for the specification of the diseased position to sample the brightness of the slave manipulator tip part from the in vivo data reconstructed in the image such as image, data given by a MRI, X-ray CT and ultrasonic CT, and to make it audible.

Figure 22:
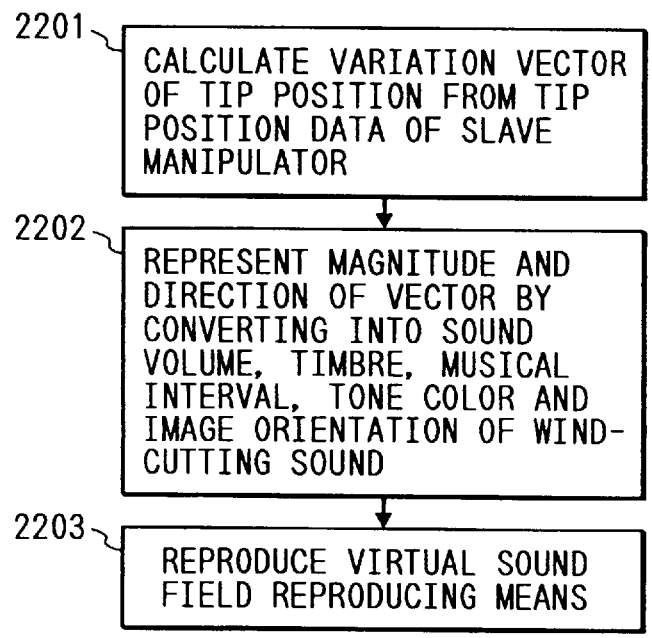
FIG. 22 is a flow chart showing an example of an algorithm for translating the motion of the manipulator into effective sound.

It may be also preferable to generate effect sound for making the motion of the slave manipulator within the environment comprehensible and to generate onomatopoeic words and mimetic words for explaining the situation in the same time. FIG. 22 shows one example thereof.

In FIG. 22, a time derivative of a position vector of the tip or a variation vector between sampled times is calculated from the 115 position data in Step 2201. Then, the magnitude and direction of the vector are represented by sound volume, timbre, musical interval, tone color and image orientation of a wind-cutting sound in Step 2202 and is reproduced by the virtual sound field reproducing means 2101 in Step 2203.

The virtual sound field generated by the work environment data processor 201 as described above is presented to the operator by the virtual sound field reproducing means 210. Thereby, the use of the sound field allows the realism to be added further and each surgical operator to operate more readily.

Figure 23:
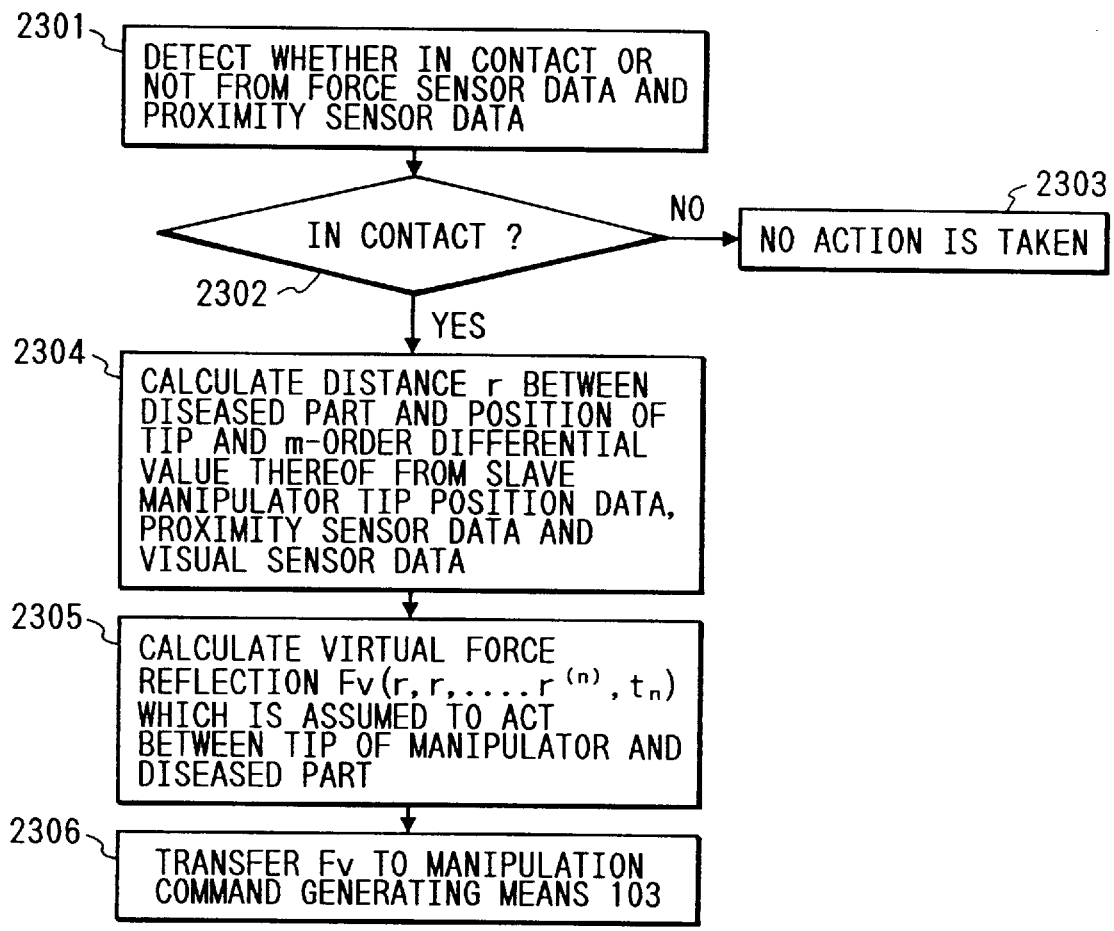
FIG. 23 is a flow chart showing an example of an algorithm for generating virtual force reflection from distance.
Figure 24:
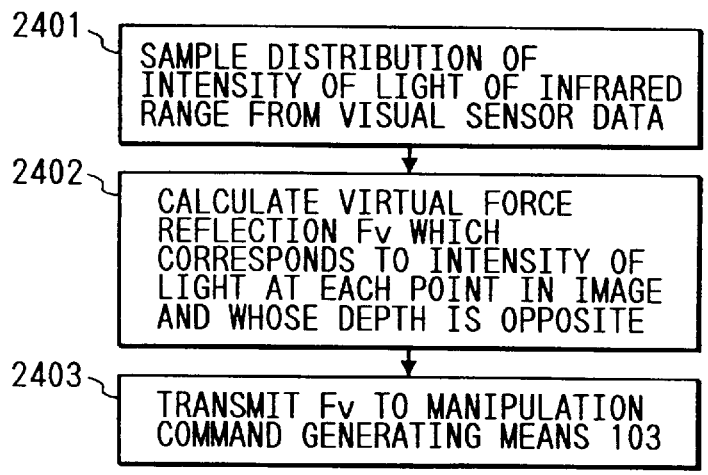
FIG. 24 is a flow chart showing an example of an algorithm for generating virtual force reflection from the distribution of temperature.

A process for generating the virtual force reflection data 108 will be explained below with reference to FIGS. 23 and 24. FIG. 23 shows one example thereof. At first, it is detected and determined whether the tip of the slave manipulator is in contact or not from the force sensor data 105 and 106 in Steps 2301 and 2302. No action is taken in Step 2303 when the slave manipulator is not in contact. When the slave manipulator is in contact, a distance r between the diseased part and the tip position and m-order differential value or m-order difference value (m=1, 2, . . . ) thereof are calculated in Step 2304:

$$r^{(1)} = (dr/dt)t_n$$

$$r^{(2)} = (d^2r/dt^2)t_n$$

$$(\cdot)$$

$$(\cdot)$$

where $t_n$ is a n (=0, 1, 2, . . . )-th sampling time and $(\cdot) t_n$ indicates a value of a variable in the time $t_n$.

Next, virtual force reflection Fv (r, $r^{(1)}$, $r^{(2)}$ . . . ) which acts between the tip of the manipulator and the diseased part is calculated in Step 2305.

Then, the virtual force reflection data 108 is transmitted to the manipulation command generating means 103 in Step 2306. For example, a potential is set which will create a large virtual repulsive force when the distance between the diseased part and the slave manipulator is short.

Thereby, it allows a discontinuity of force reflection between the in-contact state and the non-contact state which might otherwise be felt by the operator to be avoided, so that the operator can manipulate the manipulator without being conscious of the transition of the in-contact and non-contact states, and so the operability is enhanced.

A process for generating virtual force reflection corresponding to a distribution of temperature will be explained below with reference to FIG. 24.

A distribution of intensity of light of an infrared range is sampled from the visual sensor data 107 in Step 2401. Next, considering that the distribution of intensity is equal to the distribution of temperature, a virtual force reflection Fv, which corresponds to the intensity of light at each point of the image and whose depth direction is opposite, is calculated in Step 2402. It is then transmitted to the manipulation command generating means 103. Thereby, this allows a contactless palpation of sensing a degree of temperature by a magnitude of the force reflection.

A method for calculating the virtual force reflection Fv is the same as that described before. However, it becomes impossible to distinguish which value is indicated if the generated virtual force reflection and the virtual force reflection obtained by the process in FIG. 23 are generated and output at the same time. Accordingly, it is preferable to set which value is indicated in advance by switching modes for example.

The provision of the virtual force reflection of the tip of the manipulator or the virtual force reflection indicating a temperature of the diseased part to the surgical operator allows a realism to be added further and the surgical operator to manipulate the manipulator more readily.

Further, an operation which can be referred to as a so-called contactless palpation may be performed by taking out the in vivo data reconstructed in the image, such as the brightness at the tip of the manipulator of the image data given by a MRI, X-ray CT and ultrasonic CT, instead of the intensity of light in the infrared wavelength range, and by converting it into a force reflection by the method described above. This is very effective from the aspects of the specification of the diseased position and of the readiness of operation.

As described above, the work environment data processor 201 superimposes and processes the force sensor data 105, the proximity sensor data 106, the visual sensor data 107, the position data 115 and the visualized in vivo data 122 reconstructed in 3-D, and based on them, converts the quality of the data or generates new data.

That is, it converts the quality by converting a physical quantity which cannot be originally sensed by human sensitive organs into what can be sensed by a human, adjusts the range by modifying a physical quantity which is out of the range detectable by human sensitive organs to a value within the range, and so to speak, replaces the sensitive organs by converting a quantity which is difficult to comprehend intuitively, though detectable by the human sensitive organs, into a quantity which is more comprehensive by detecting it in another way. Thereby, the realism of the surgery can be controlled and the operability of each surgical operator can be enhanced.

Figure 3:
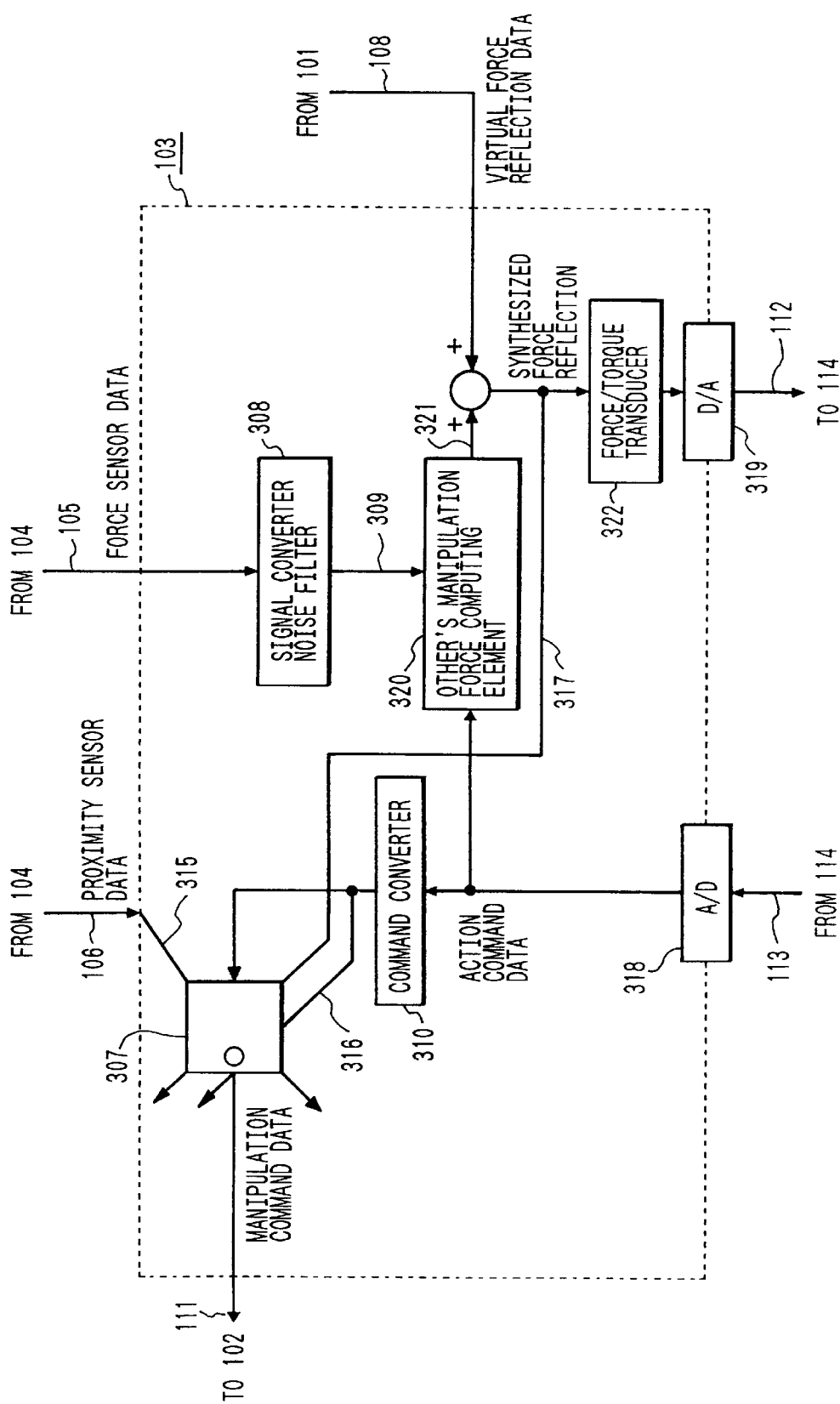
FIG. 3 is a block diagram showing one structural example of manipulation command generating means.

Next, the manipulation command generating means 103 will be explained below. FIG. 3 is a block diagram showing a structure of the manipulation command generating means 103 which comprises a virtual switch 307 for controlling a transfer of an action command, a force sensor data operating section 308 for amplifying the force sensor data 105 so as to convert it into an adequate range and for performing a recursive calculation which corresponds to removal of noise to output actual force reflection data 309, a command converter 310 for setting an action mode/control mode from the action command data 113 and for taking in each joint data from the action command inputting means 114, an A/D converter 318, a D/A converter 319, an other's manipulation force computing element 320 for giving a value obtained by adding and converting a weighted quantity of manipulation (e.g., manipulation force) of each surgical operator other than oneself to that surgical operator as a force reflection and a force/torque transducer 322. Arrows in the figure indicate flows of a signal or data.

There are a number of channels for the signals of the synthesized force reflection 112 and the action command 113 equal to a number of the action command inputting means 114 and the force sensor data 105, 106 and the virtual force reflection data 108 have a number of channels, equal to a number of slave manipulators in the diseased tissue manipulating means 102, and these channels are multiplexed.

An operation of the force sensor data operating section 308, the other's manipulation force computing element 320 and the force/torque transducer 322 will be explained below with reference to FIGS. 25 and 26.

Figure 25:
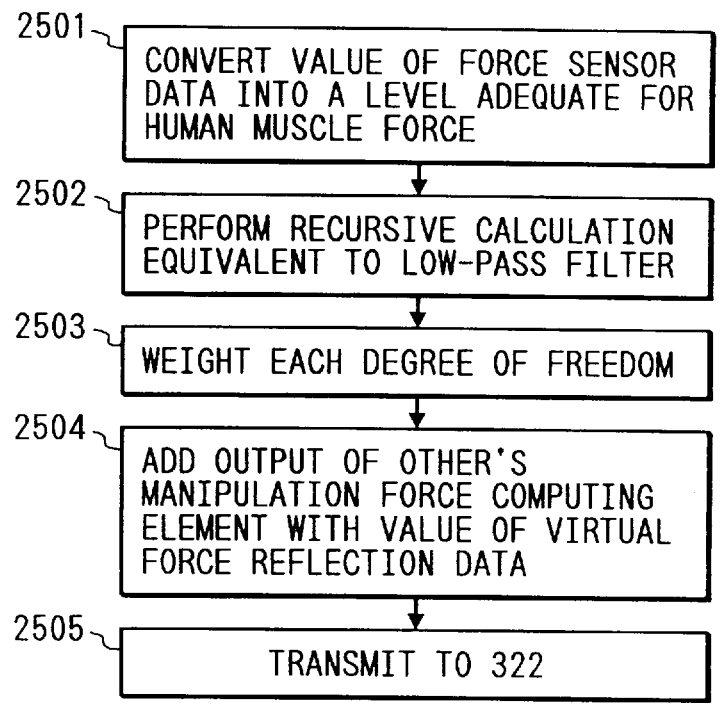
FIG. 25 is a flow chart showing an algorithm for operating a force sensor data operating section.

In FIG. 25, the force sensor data operating section 308 converts the magnitude of the force sensor data 105 into an adequate level for human muscle force in Step 2501 and performs a recursive calculation equivalent to a low-pass filter to remove noise in Step 2502.

Then, after weighting each degree of freedom in Step 2503, it adds an output 321 of the other's manipulation force computing element 320 and the value of the virtual force reflection data 108 to generate synthesized force reflection data in Step 2504 and inputs it to the force/torque transducer in Step 2505.

Figure 26:
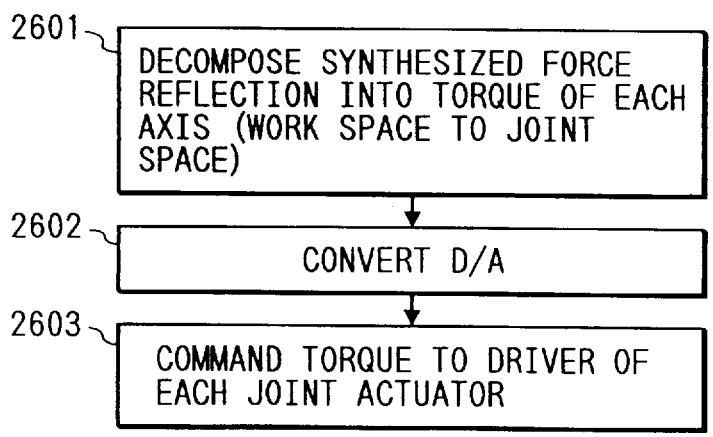
FIG. 26 is a flow chart showing an algorithm for translating synthesized force reflection.

The force/torque transducer 322 converts the synthesized force reflection data into each joint torque value of a force reflection generating section of the action command inputting means 114 in Step 2601 and outputs it as analog data through the D/A converter 319 as shown in FIG. 26.

The output is transmitted to the action command inputting means 114 and becomes a torque command of a driver of each joint actuator in Step 2603.

The above-mentioned process is performed by a number of the action command inputting means 114, i.e., a number of channels. An operation of the other's manipulation force computing element 320 will be explained later in detail.

Figure 27:
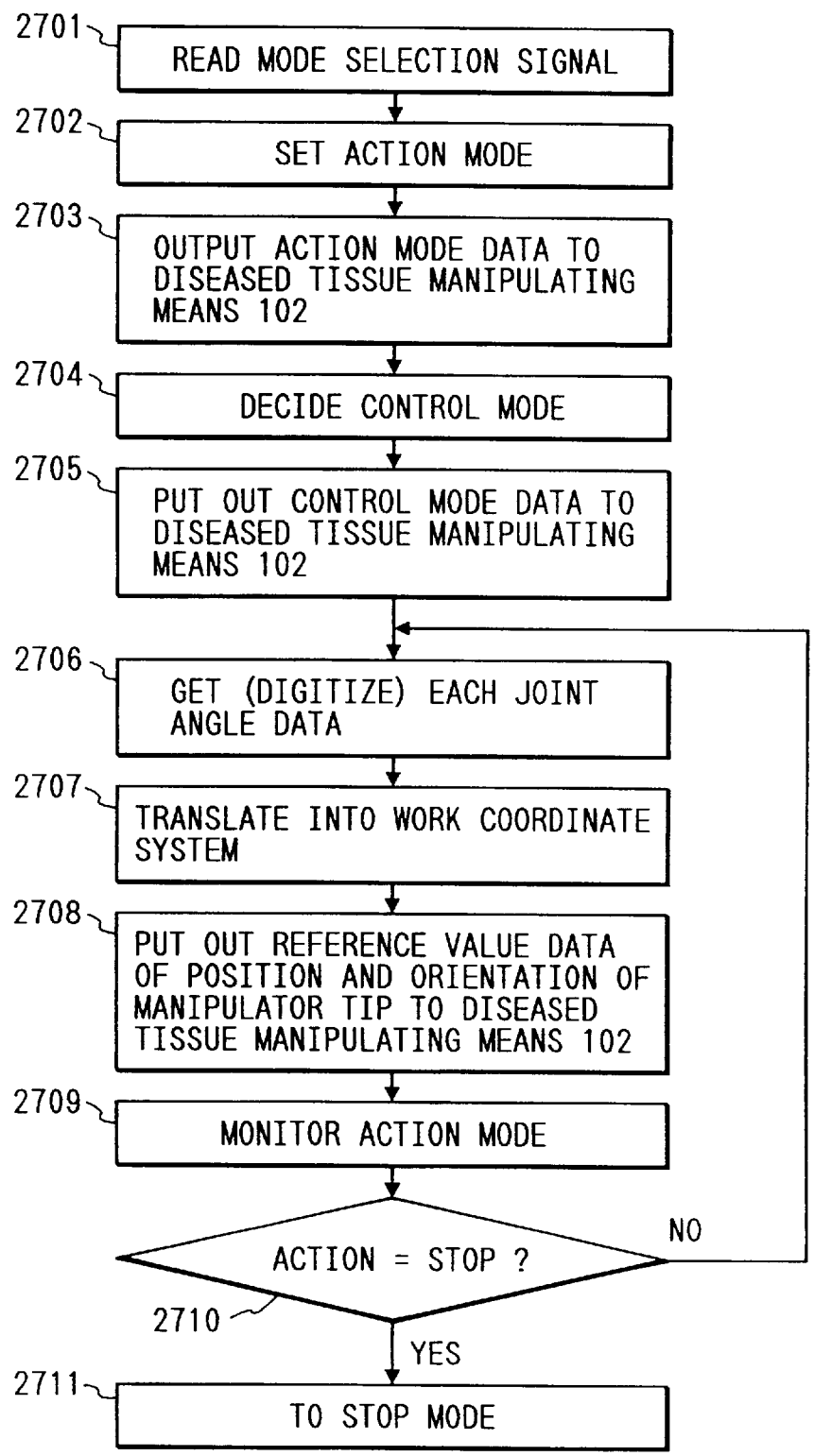
FIG. 27 is a flow chart showing an algorithm for operating a command converting section.

An operation of the command converter 310 will be explained below with reference to FIG. 27.

The command converter 310 reads a mode selection signal which is contained in the signal from the action command inputting means 114 in Step 2701. It sets an action mode in Step 2702 and outputs the action mode to the diseased tissue manipulating means 102 in Step 2703.

Then, it selects a control mode based on the action mode in Step 2704 and puts out the control mode to the diseased tissue manipulating means 102 in Step 2705. Some control modes are not permitted depending on the action mode, so that the control mode is determined in Step 2704 by automatically selecting from modes other than an unpermissible control mode in accordance to an adequately set algorithm or is determined by inputting a mode selection from the action command inputting means 114.

After selecting the control mode and outputting it to the diseased tissue manipulating means 102, each joint angle data is obtained through the A/D converter 319 in Step 2706 and is translated into a work coordinate system in Step 2707.

After putting out manipulator tip position reference value data to the diseased tissue manipulating means 102 in Step 2708, the action mode is monitored in Step 2709 and if the action mode is "Stop", the process advances to a stop mode, and if it is not, the process returns to Step 2706 in Steps 2710 and 2711.

A train of data transmitted to the diseased tissue manipulating means 102 comprises a header 2801, an action mode indicator 2802, a control mode indicator 2803 and a train of data of indicating position and orientation 2804 until an arbitrary time tn. The data is transmitted to the diseased tissue manipulating means 102 sequentially.

Figure 29:
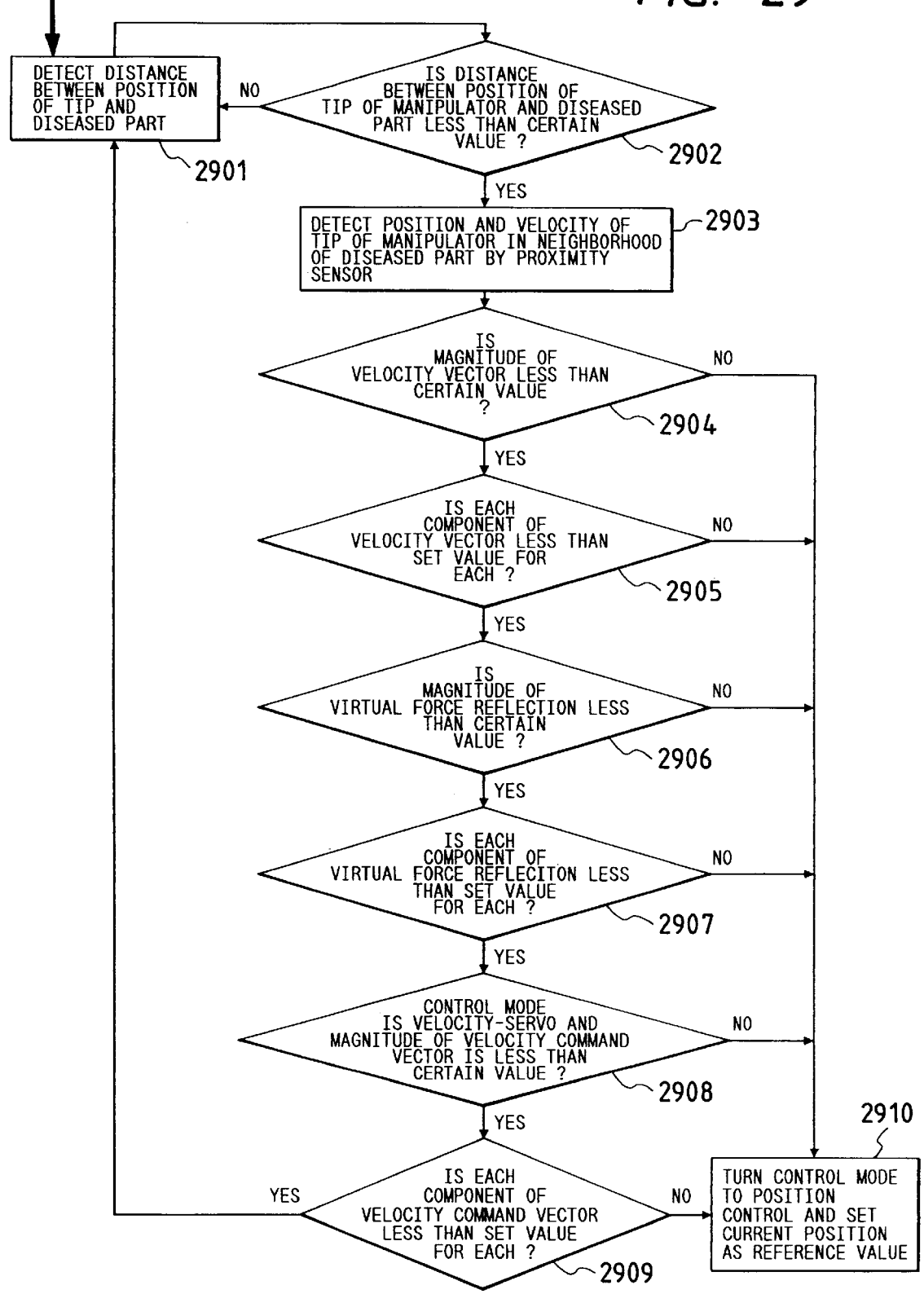
FIG. 29 is a flow chart showing an algorithm for operating a virtual switch.

Next, the operation of the virtual switch 307 will be explained with reference to FIG. 29 which shows an operating algorithm thereof. In the figure, the distance between the position of the tip of the manipulator and the diseased part is detected in Step 2901 and is checked to determine whether it is less than a certain value or not in Step 2902. If it is not less than the certain value, the process returns to Step 2901.

When it is less than the certain value, the position and velocity of the tip of the manipulator in the neighborhood of the diseased part are detected by the proximity sensor in Step 2903.

Next, the magnitude of the velocity vector and the magnitude of each component thereof, the magnitude of the virtual force reflection and the magnitude of each component thereof and the magnitude of a velocity command vector and the magnitude of each component thereof, when the control mode is velocity-servo, are checked, and if they are all less than the certain value, the process returns to Step 2901, and if any one of the conditions is not met, the control mode is turned to position control and the current position is set as a command value in Steps 2904 through 2910.

The above-mentioned process is performed for all the channels. Thereby, the command value will not be changed when an abnormality occurs, thus enhancing the safety of the operations.

The action command inputting means 114 will be explained below with reference to FIG. 30. Even if a plurality of the action command inputting means 114 are used, the structure thereof is the same. It comprises a magnet 3001 for coupling grip and force reflection generating section, a grip constraining solenoid controlling signal 3002 and a coupling electromagnet current controlling signal 3003, a grip constraining solenoid 3004, an action mode switching switch 3006, a grip 3007, a globular coupler 3008, spherical joints 3009 and direct acting cylindrical electrostatic actuators 3010.

The synthesized force reflection 112 decomposed per each actuator and output from the manipulation command generating means 103 is applied to each actuator as control input 3011.

Each actuator 3010 is driven by it and generates a required force reflection as a whole. Displacement of each actuator 3010 is detected by a displacement sensor not shown and is output as a displacement sensor output 3012.

Each surgical operator holds the grip 3007 and moves it while sensing force reflection to input action data. The mode is switched by manipulating the action mode switching switch 3006 on the grip to output an action mode setting signal 3005. At this time, the globular coupling 3008 between the grip 3007 and the force reflection generating section is coupled by the magnetic force of the electromagnet.

The coupler 3008 is constructed so as to be controlled by the grip constraining solenoid controlling signal 3002 and the coupling electromagnet current controlling signal 3003 from the magnetic force controlling means 3001 in accordance to the action mode and the magnitude of input and to be able to change a constraint in terms of a degree of freedom.

Figure 35:
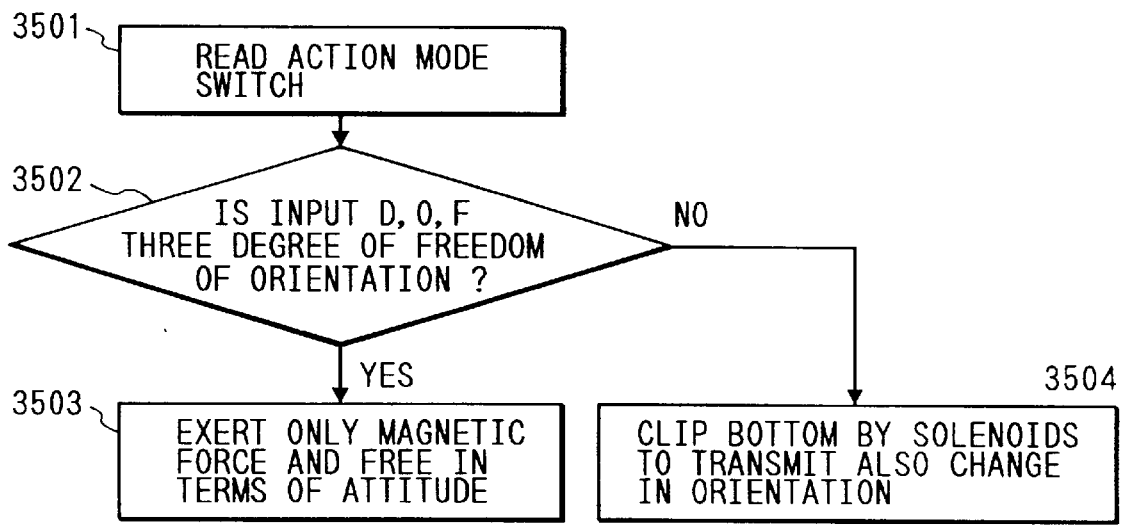
FIG. 35 is a flow chart showing an example of an algorithm of magnetic force controlling means.

FIG. 35 is a flow chart showing the operation of the magnetic force controlling means 3001, which reads the action mode switch in Step 3501 and when the action mode is a mode which instructs only position in Step 3502, it exerts only the magnetic force of the electromagnet in Step 3503.

Figure 30:
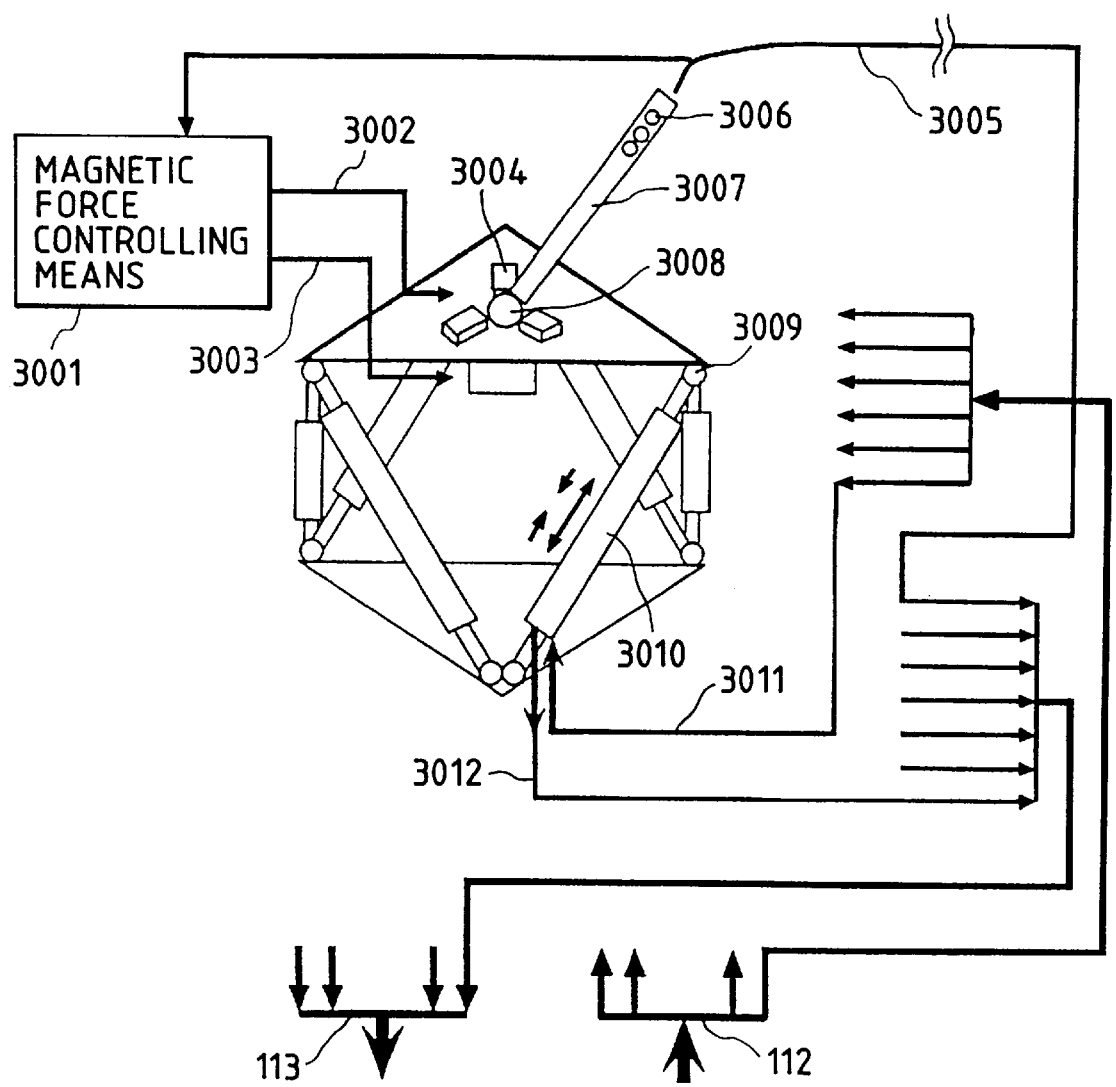
FIG. 30 is a block diagram showing one structural example of action command inputting means.

Because the coupler 3008 is globular as shown in FIG. 30, it is free in terms of its orientation. In other words, only three degrees of freedom of position can be instructed by manipulating the grip 3007.

On the other hand, a change in the orientation can be instructed by clipping the bottom of the grip by the solenoids 3004 when all six degrees of freedom of position and orientation are to be instructed, as indicated in Step 3504 in FIG. 35.

When an excessive force or moment is applied in the state wherein the joint composed of the coupler 3008 and the solenoids 3004 is fixed, the constraint is released. Thereby, it becomes possible to prevent an instruction from being input with excessive force, thus enhancing the safety of the manipulation. The direct acting cylindrical electrostatic actuator 3010 will be explained later.

Thereby, no command value is transmitted to the diseased tissue manipulating means 102 when an abnormality occurs, thus enhancing the safety of the operation.

Figure 38A:
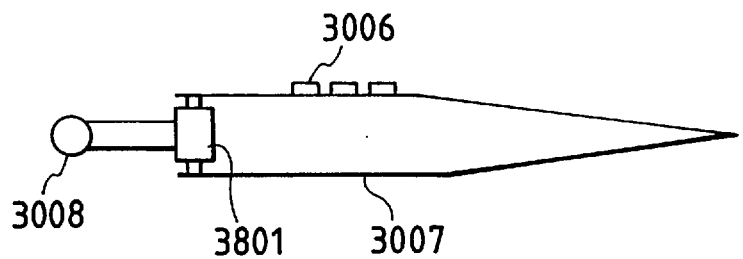
FIG. 38($a$) to 38($c$) are is schematic drawings showing examples of a grip portion in the action command inputting means.
Figure 38B:
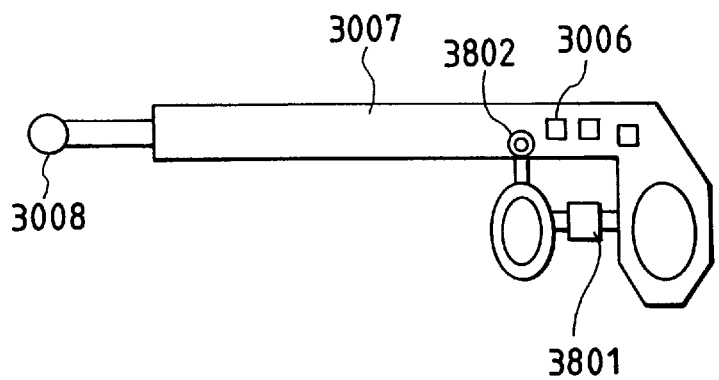
Figure 38C:
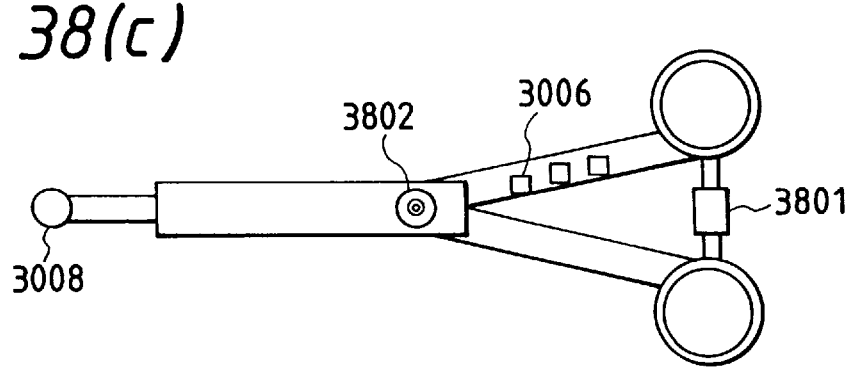

It is noted that the grip 3007 may be as shown in FIGS. 38(*a*)–38(*c*), beside the pen-type grip shown in FIG. 37. FIG. 38*a* shows a pincette-type grip, FIG. 38*b* a ligator-type grip and FIG. 38*c* a clamp-type grip. The operator can manipulate any one of them while sensing the force reflection generated by the grip force reflection generating actuator 38001.

In FIGS. 38*b* and 38*c*, one side or both sides of part of the grip for hooking fingers rotate on an axis of rotation 3802. The operator can replace the grip 3007 by releasing both the clipping and magnetic force caused by the solenoids 3004 at this time. That is, the operator can attach/remove the grip corresponding to the circumstance to input action commands.

When a conduction is detected in the joint as the operator replaces the grip 3007, an initial signal corresponding to the shape of the grip is transmitted to the diseased tissue manipulating means 102 via the manipulation command generating means 103 and a manipulator having a tool corresponding to that as an effector is assigned. Accordingly, it is just necessary to provide several kinds of tools for this part and it is not necessary to provide the action command inputting means with a number of tools in advance.

Thereby, the operator will not be confused as to which tool can be used by using which input means. Further, because one input means will do for one hand, the space at the hand can be wide open.

Figure 39:
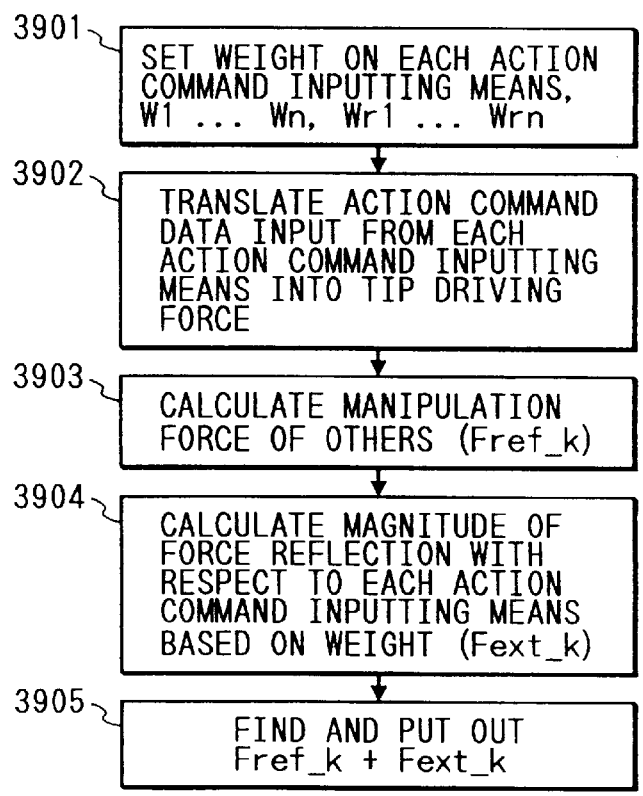
FIG. 39 is a flow chart showing an operation algorithm of a computing element of manipulated force by another.

The other's manipulation force computing element 320 will now be explained below with reference to FIG. 39. Assume a case when a plurality of the action command inputting means 114 are assigned to one slave manipulator. When that number is n, weights $W_1$ through $W_n$ are set on each action command inputting means at first in Step 3901:

$$W_1 = W_2 = \ldots W_n = 1; \; W_k \geq 0 \, (k=1 \text{ to } n).$$

Further, assuming a case when force feedback is implemented, weight is also set with respect to force reflection from an object of work. This is considered as $Wr_1$ to $Wr_n$ and set in the similar manner with the above as follows:

$$Wr_1 = Wr_2 = \ldots Wr_n = 1; \; Wr_{k\geq} = (k=1 \text{ to } n).$$

The magnitude of Wk indicates which action command inputting means is dominant.

Next, action command data 113 input from each action command inputting means is converted into a force in Step 3902. While it is not necessary to convert the data when the mode at this time is a force command mode, a value which is obtained by inputting an error between a command and a response to an adequate transfer function is used as a tip driving force command value when the command value is position, velocity or the like. Those values are a vector quantity having a magnitude and direction and are set as f1 through fn. At this time, among the force reflection given to the k-th (k=1 to n) action command inputting means, one which is caused by manipulation force by others is calculated in Step 3903. When it is set as $\text{Fref}_k$, it may be expressed as follows:

$$\text{Fref}_k = W_1 f_1 + W_2 f_2 + \ldots + W_{k-1} f_{k-1} + W_{k+1} f_{k+1} + \ldots + W_n f_n$$

When force feedback is implemented, force reflection $\text{Fext}_k = Wr_k * \text{Fext}$ given to the k-th (k=1 to n) action command inputting means is calculated in Step 3904 where Fext is the force sensor data 105 and is a vector quantity.

It is normally considered that it is natural to set $W_k = Wr_k$ (k=1 ... n) in the above-mentioned process. That is, it is a method of returning a large portion of force reflection to more dominant input means. However, it is not always necessary for $W_k = Wr_k$ in general and an anisotropy may be given with respect to direction. That is, $W_k$ and $Wr_k$ can be expressed in a matrix. In that case, it follows:

$$W_1 + W_2 + \ldots W_n = I; \; W_k^t W_k \geq 0$$

where the superior letter t indicates transposition of the matrix and I is a unit matrix. The same applies also to Wrk. Finally, $\text{Fref}_k$ and $\text{Fext}_k$ are added and output in Step 3905. This data is synthesized with the virtual force reflection data 108.

The algorithm described above allows the operators who input action from different input means to perform operation while sensing the force generated by the others and the force reflection from the object.

It then is possible to teach how to handle a surgery "bodily" for example and to transfer surgical techniques by combining them with surgical simulations.

Figure 4:
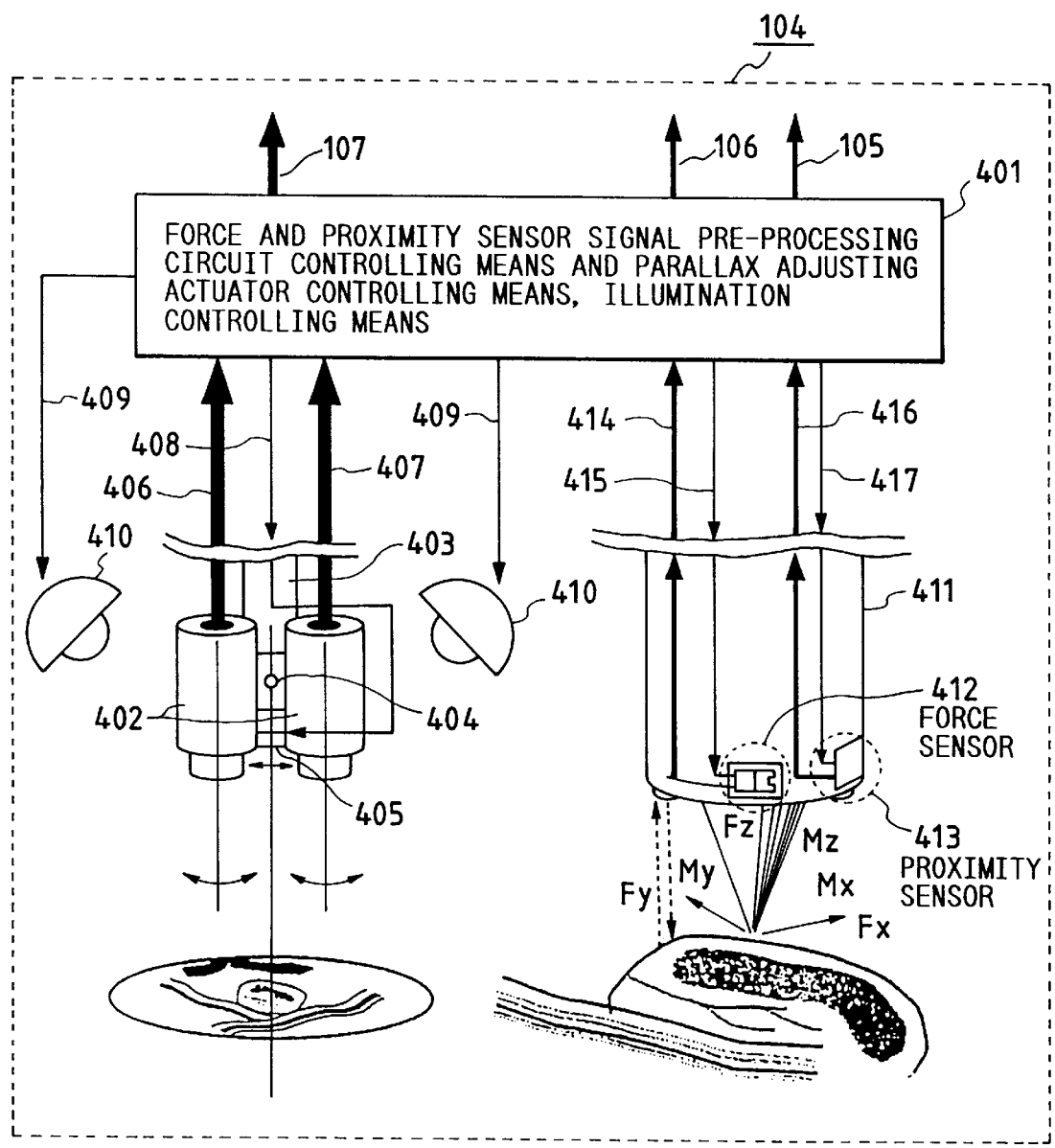
FIG. 4 is a block diagram showing one structural example of working environment data detecting means.

The work environment data detecting means 104 will be explained below with reference to FIG. 4.

The work environment data detecting means 104 comprises visual sensors 402, a visual sensor mounting section 403, a passive rotary joint 404 for linking the both of them, a linear actuator 405 for adjusting the angle of parallax, an illumination 410 for illuminating the diseased part, a force sensor and force sensor signal pre-processing circuit 412, a proximity sensor and proximity sensor signal pre-processing circuit 413 attached at the tip portion of the slave manipulator. It further comprises operation controlling means 401 for taking in an image signal for the right-eye 406 and an image signal for the left-eye 407 to generate and output the visual sensor data 107, for generating and outputting control signals 408 and 409 of the linear actuator 405 and the illumination 410, for taking in a force sensor signal 414 and a proximity sensor signal 416 to control the sensors by a force sensor signal pre-processing circuit controlling signal 415 and a proximity sensor signal pre-processing circuit controlling signal 417 and for outputting the force sensor data 105 and the proximity sensor data 106.

The visual sensors 402 take in an image of the diseased part and output the image signals for the right-eye and the left-eye 406 and 407. The visual sensors 402 are linked to the mounting section 403 via the passive rotary joint 404.

The image signals 406 and 407 are digitized and turned into the visual sensor data 107 in the operation controlling means 401. The force sensor signal 414 and the proximity sensor signal 416 are also converted into digital values to turn to the force sensor data 105 and the proximity sensor data 106. Here, the operation controlling means 401 controls each part by an algorithm as shown below.

Figure 32:
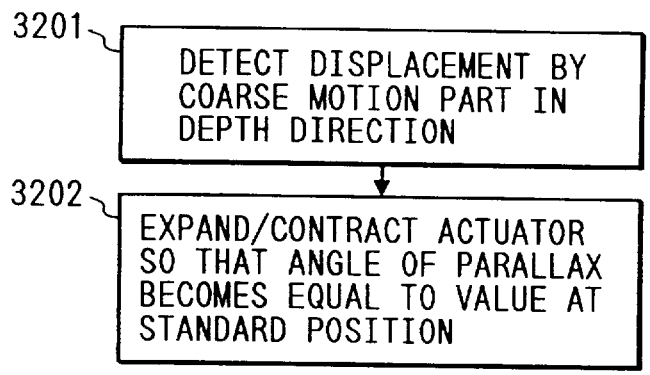
FIG. 32 is a flow chart showing an algorithm for controlling an actuator for controlling an angle of parallax.

First, as shown in FIG. 32, when it detects a quantity of movement of a coarse motion part 503 (see FIG. 5, described later) of the diseased tissue manipulating means 102 in the depth direction of the diseased part in Step 3201, it sends the control signal 408 to the linear actuator 405 so that the angle of parallax of the right and left visual sensors becomes equal to a value at the reference position in Step 3202. Then, the angle of parallax can be maintained constant as the linear actuator 405 expands/contracts and the right and left visual sensors 402 rotate finely and equally centered on the passive rotary joint 404.

Figure 33:
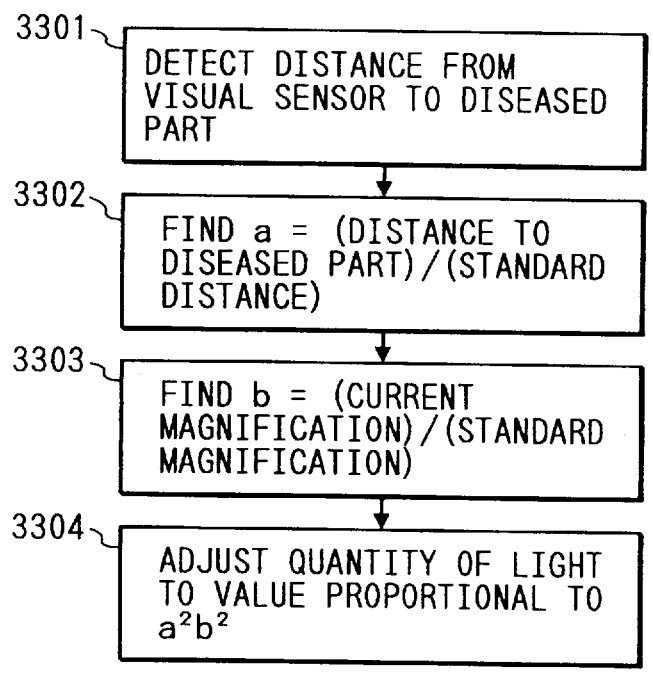
FIG. 33 is a flow chart showing an algorithm for controlling illumination.

It also controls the brightness of the illumination 410 by detecting a distance from the visual sensor to the diseased part in Step 3301 in FIG. 33 to find:

a=(distance to diseased part)/(standard distance)
in Step 3302. It then finds:

b=(current magnification)/(standard magnification)
in Step 3303. Finally, it adjusts the quantity of light to a value proportional to a2×b2 in Step 3304. The process in FIGS. 32 and 33 described above allow the angle of parallax and the brightness of the diseased part to be adjusted adaptively corresponding to the distance between the diseased part and the visual sensor and the magnification when they change.

Figure 31:
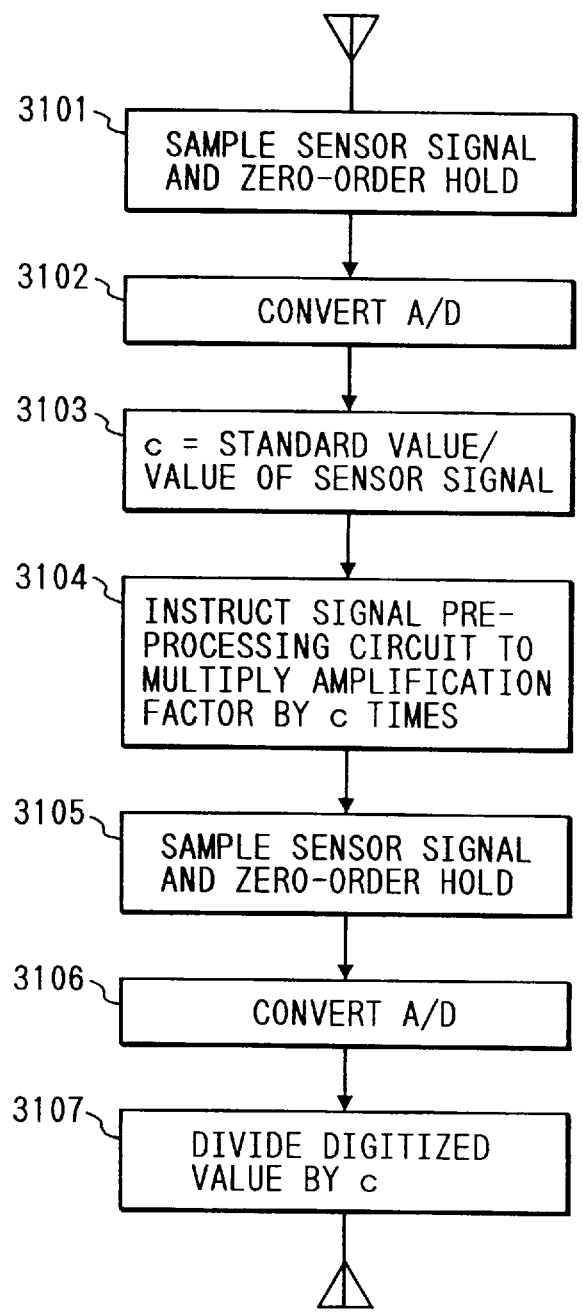
FIG. 31 is a flow chart showing an algorithm for processing signals of the force sensor.

The force sensor and the pre-processing circuit 412 thereof and the proximity sensor and the pre-processing circuit 413 thereof are mounted at the tip 411 portion of the slave manipulator. The small force and proximity sensors and the signal processing circuits thereof may be manufactured by micro-machining technology. While the force sensor outputs the force sensor signal 414 and the proximity sensor outputs the proximity sensor signal 416, respectively, the operation controlling means 401 sends the control signals 415 and 417 to each processing circuit corresponding to a signal level to change the amplification factor at that time. A digital signal of several bits having a higher voltage as compared to a noise level assumed to be brought about there is used for the control signal and a control process as shown in FIG. 31 is carried out.

An amplifier output within the above-mentioned processing circuit is sampled and zero-order-held in Step 3101 and is converted from analog to digital in Step 3102. Then, c=(standard value of sensor signal)/(value of sensor signal) is found in Step 3103.

Next, the operation controlling means 401 instructs the pre-processing circuit to multiply the amplification factor by c times in Step 3104. The processing time between the Steps 3101 and 3103 is very short and it is assumed that the value of the signal will not change during that time.

The above-mentioned amplifier output is again sampled and zero-order-held in Step 3105 and is converted from analog to digital in Step 3106. Then, the digitized value is expressed by a real number and is divided by c in Step 3107. That is, when the signal level is small, the amplification factor of the pre-processing circuit is increased to prevent the signal from being buried by the noise which is mixed in until it is input to the operation controlling means 401, and when the signal level is large, the amplification factor is reduced to prevent the signal from saturating. Thereby, it becomes possible to reduce the effect of the noise from the surrounding environment and the actuator and to reduce the effect of quantization due to the digital sampling.

The diseased tissue manipulating means 102 will now be explained.

Figure 5:
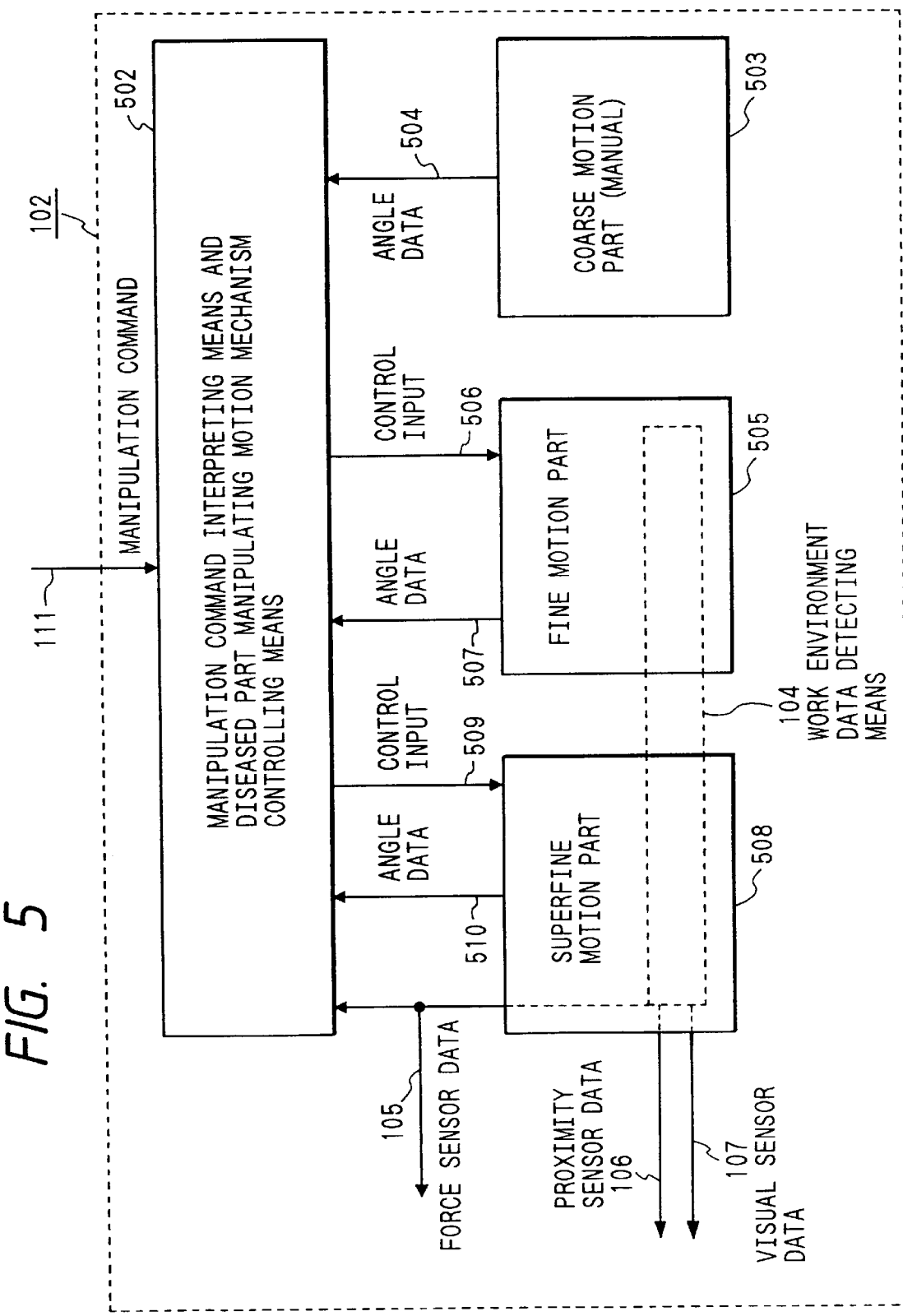
FIG. 5 is a block diagram showing a whole structure of diseased tissue manipulating means.

As shown in FIG. 5, it comprises manipulation command interpreting and controlling means 502, the coarse motion part 503, the fine motion part 504 and the superfine motion part 508 as a whole.

Each part is manufactured by using only a material which receives almost no force from a magnetic field, as compared to the type of structural material, often used, such as polymeric materials like plastics.

Thereby, the diseased tissue may be manipulated without being influenced by the magnetic field even when MRI is used as one of the structural element of the in vivo data measuring means 117 described later. Or, conversely, because in vivo data created by the MRI can be obtained during operation, i.e., during a time when the diseased tissue is manipulated, it becomes possible to pursue any deformation in the tissue surrounding the diseased part in real-time and to perform operations while measuring functions in addition to shape especially in craniotomy for example.

The superfine motion part 508 has a plurality of manipulators and various treatment effectors may be attached to the tip thereof.

It is determined in advance which manipulator should be activated in a certain circumstance by the signal from the manipulation command generating means 103. The manipulation command 111 comprises a command whose degree of abstraction is high, such as "grasp", a control mode and a train of time-series motion command data of the tip of one manipulator.

Receiving the train of data, the manipulation command interpreting and controlling means 502 interprets it and generates motion commands of each joint of the 505 and the manipulator (a plurality of manipulators if necessary) of the superfine motion part 508 and makes a servo-level primitive control in the same time from the grasp command, the control mode and the motion command value of one manipulator.

Control input 506 to each joint of the fine motion part 505 and control input 509 to each joint of the superfine motion part 508, and the end effector are determined by using the above-mentioned manipulation command, displacement sensor data at each part 504, 507 and 510 and the force sensor data 105.

Figure 34:
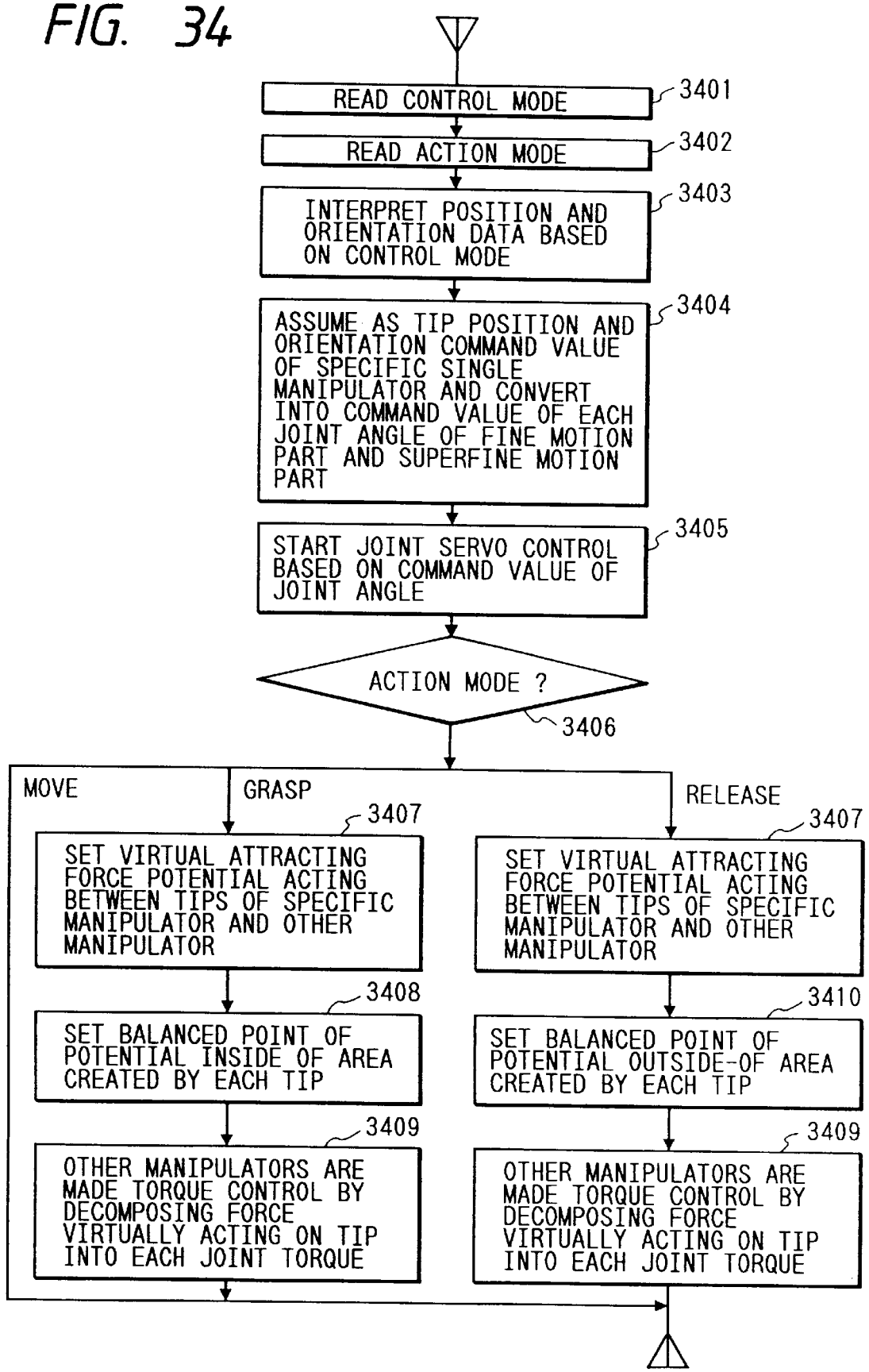
FIG. 34 is a flow chart showing an example of an algorithm for executing interpretation.

FIG. 34 shows an operation flow of the manipulation command interpreting and controlling means 502.

Figure 28:
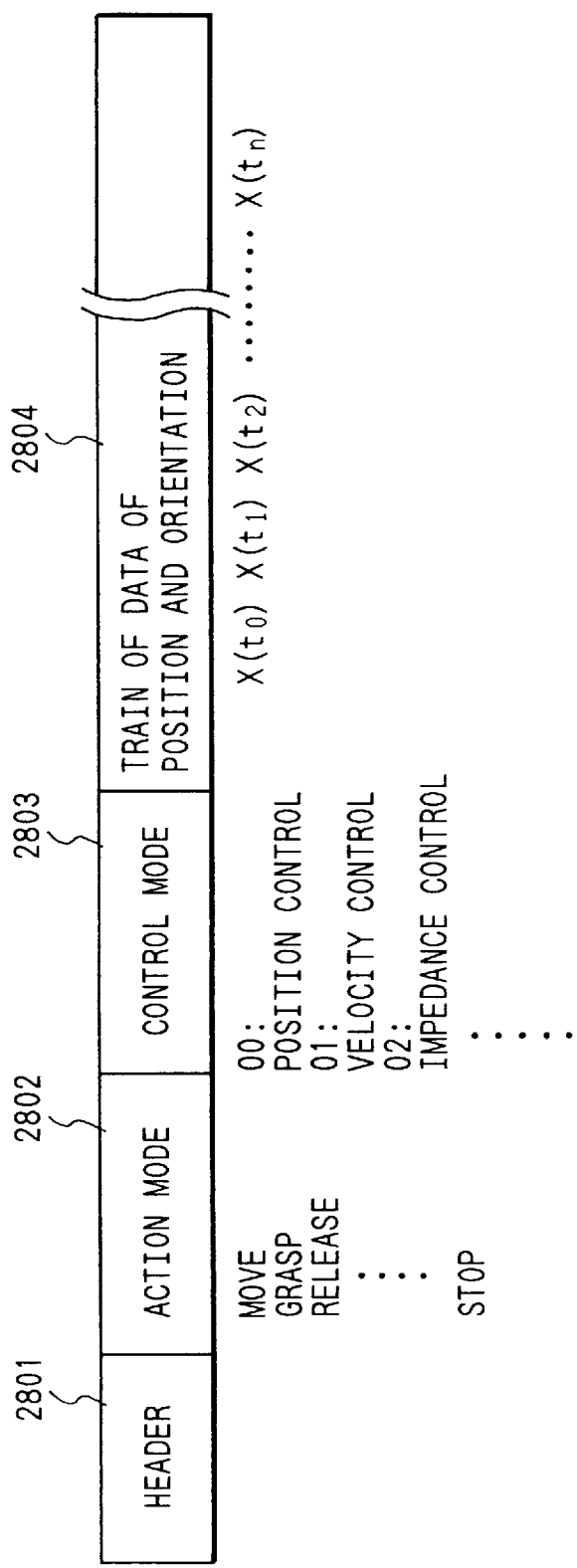
FIG. 28 is a diagram showing a data format of manipulation command data.

At first, it reads the control mode and the action mode from data transmitted in the sequence as shown in FIG. 28 from the manipulation command generating means 103 in Steps 3401 and 3402 and interprets the train of position and orientation data based on the control mode in Step 3403.

The control mode specifies a control scheme, such as position control/velocity control/impedance control, an instructed number indicating the degree of freedom and existence of anisotropy related to the degree of freedom.

Assuming then that the above-mentioned commands and specifications are tip position and orientation command values of a specific single manipulator, it converts them into command values of each joint angle of the motion parts 505 and 508. Here, a quantity of displacement of a direct acting joint will be also referred to as an angle.

Next, the controlling means 502 performs joint servo control of the specific manipulator based on the command value in Step 3405. The process is branched here in accordance with the action mode in Step 3406, and if the mode is MOVE, the process is finished.

When the action mode is GRASP, a virtual attracting force potential which acts between tips of the specific manipulator (the manipulator to be manipulated by the train of position and orientation data) and the other manipulator is set in Step 3407 and a balanced point of the potential (point where the attracting force becomes zero) is set within a space created by the tip of each manipulator in Step 3408.

The other manipulator decomposes the force which virtually acts on the tip the to torque of each joint to control the torque in Step 3409.

When the action mode is RELEASE, the action is almost the same with that of GRASP except that the balanced point of the potential is set outside of the above-mentioned space in Step 3410.

Although only three types of action modes have been exemplified, as described above, it is necessary to provide several more types of basic action modes in reality. Then, a mode, in which a master manipulator and a slave manipulator correspond one-to-one in controlling position/force, which is being practiced conventionally, and a mode, in which a plurality of master manipulators correspond to one slave manipulator, are provided and are switched according to circumstances.

Figure 6:
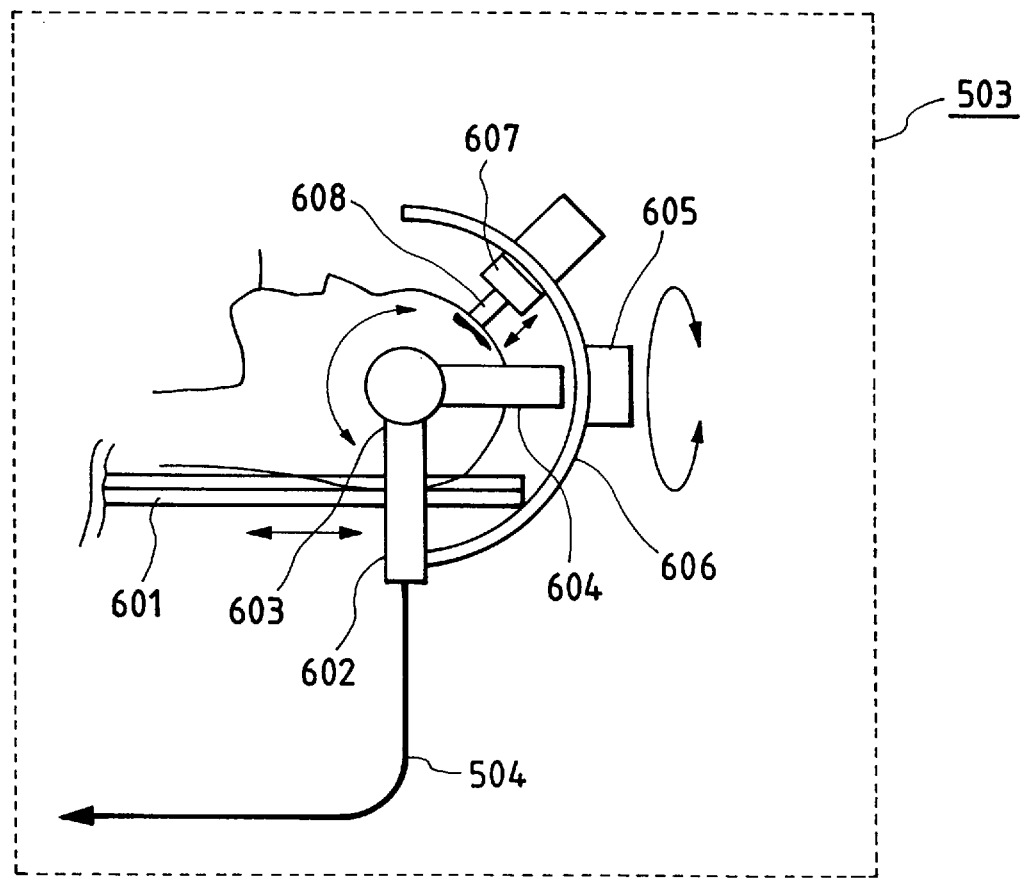
FIG. 6 is a schematic diagram showing a structural example of a coarse motion part.

The coarse motion part 503 will now be explained with reference to FIG. 6. The coarse motion part 503 comprises a pedestal 601, a first link 602, a first joint 603, a second link 604, a second joint 605, a third link 606 and a third joint 607 and a part 608 is provided at the third joint 607.

The pedestal 601 is coupled as a the first link 602 with a linear motion rail, and the mechanism of the first link thereafter may be moved horizontally along the transverse direction of the pedestal 601. The degree of freedom of this part is manually set and a mechanical lock is provided so as to be able to secure it at any position.

By constructing the part of the mechanism of the first link and thereafter to allow it to be manually moved, it becomes possible to deal quickly with an emergency, such a as power failure, thus enhancing the safety.

Although the shape of the first link 602 is semi-circular, it is not always necessarily to be semi-circular so long as it does not interfere with the mechanism of the second link and other elements.

The second link 604 is coupled with the first link 602 via the first joint 603 and rotates axially on the center line of the first joint 603 on the both sides. The first joint 603 is also constructed so as to be manually rotated and to be locked for the same reason with the case of the manual linear motion rail. The shape of the second link 604 is semi-circular.

The third link 606 is coupled with the second link 604 via the second joint 605 and rotates axially on the center line of the second joint 605. The third link 606 is also constructed so as to be manually rotated and to be mechanically locked to enhance the safety. The shape of the third link 606 is also semi-circular.

The fine motion part 608 is coupled with the third link 606 via the third joint 607. The third joint 607 moves directly in the normal direction of the third link 606.

Displacement sensor data 504 of each joint is sent to the manipulation command interpreting and controlling means 502 which has been described with reference to FIG. 5.

By constructing the device as described above, this coarse motion part system can have a mechanical and structural degree of freedom in one degree of freedom of the parallel direction and three degrees in freedom of the spherical coordinate system, which will accommodate the shape of the cranial bone of a reclining patient and allow coarse positioning of the patient in the beginning of an operation and allow removal thereof in case of emergency, for example, to be swiftly and readily effected.

Figure 7:
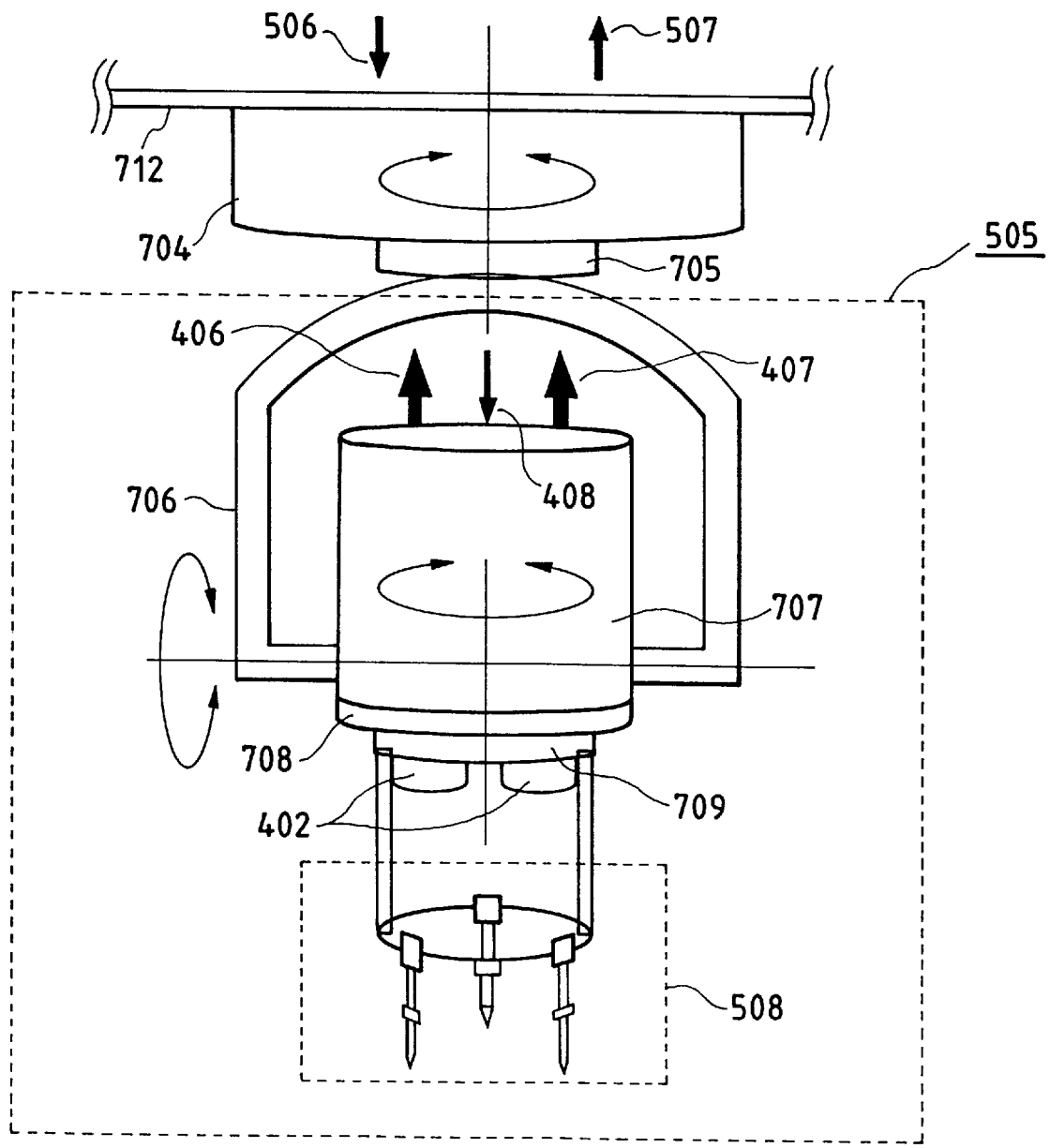
FIG. 7 is a schematic diagram showing a fine motion part.

The structure of the part 505 will now be explained with reference to FIG. 7.

The part 505 comprises a pedestal link 704, a first joint 705, a second link 706, a second joint 707, a third link 708, a third joint 709 and a base 712 of the fine motion part.

The first through third joints are all rotary joints and the construction is such that only the orientation of the whole superfine motion part is changed.

It has been pointed out that in a case of fine works, the change in orientation is independent of scaling. That is, while a small value becomes an object of the work with respect to distance, the fine work is the same as the normal work with respect to the change in orientation. Accordingly, the degree of freedom of the position and orientation can be separated and the same driving method and mechanism as those in the normal scale can be used in terms of the orientation.

The change in orientation of the superfine motion part 508 is linked with the visual sensor 402. Thereby, the focus point of the visual sensor 402 is always positioned approximately in the work space of the manipulator of the superfine motion part 508. Although the motion part 505 has had a gimbal structure in FIG. 7, a mechanism such as a Stewart platform may be used.

The superfine motion part 508 will be explained below with reference to FIG. 8.

The superfine motion part 508 comprises columns 801, a ring rail 802, a first joint 803, a first link 804, a second joint 805, a second link (tip of slave manipulator) 411 and a Peltier effect element 809.

The first joint 803 moves with two degree of freedom of linear motion in the direction of center line of the ring rail 802 and of rotation around the center line. The second joint 805 is cylindrical and rotates around its center line.

The structure described above allows the whole manipulator to be compact. While the superfine motion part 508 is constructed to have three degrees of freedom, it is possible to increase the degree of freedom by replacing the structures of the first link 804 and the second link 411 so as to have the same structure as the first joint 803. In the present embodiment, more than six degrees of freedom have been realized by adding the degrees of freedom of the superfine motion part 508 to the three degrees of freedom of rotation of the fine motion part.

The Peltier effect element 809, which is attached at the tip of the manipulator, is an element for realizing thermoelectric refrigeration by the Peltier effect which can be realized due to micro-machining technology.

If the manipulator itself is provided with a mechanical force which can destroy organic tissues, such as brain tissue, a nerve and a blood vessel, it becomes very dangerous in the event of an accident, such as a runaway. Then, it is necessary to replace cutting and peeling of diseased tissues, which has been done by mechanical force in the past, with a manipulation which causes tissues to degenerate by controlling the flow of energy in a fine surgery operation.

Further, the reduction of the required mechanical force brings about advantages in design in that the manipulator and the actuator which drives the manipulator can be miniaturized further or specifications required for them may be eased, which is very favorable.

Hitherto, while a super-high temperature method (by means of a laser knife and others) has been used as a tissue degeneration method using energy control, it affects the surroundings considerably with its radiation, leaving some anxiety about the application of such a procedure to a fine surgical operation. On the other hand, the degeneration and destruction of tissues by means of refrigeration causes only the manipulated part to degenerate reliably as almost no heat is transferred unless contact occurs.

Further, because there is not much temperature difference with the environment as compared to a laser, it is not necessary to consider the problem of radiation (though the temperature difference is opposite in this case).

A superfine motion part which is less invasive and causes less effect around it may be realized as described above.

It is noted that although it is advantageous in many points to cause degeneration and spallation of tissues by the Peltier effect element, it is not realistic to carry out all surgical treatments by cryo-spallation. Further, the treatment effector is not confined only to a Peltier effect element and those tools known from the past may be used in combination. That is, the manipulator may be equipped with a laser knife, an ultrasonic knife, or an electric knife or a small clamp, knife or clip may be attached to it.

Further, if there are a plurality of manipulators, it is possible to prepare those having different treatment effectors.

Figure 8:
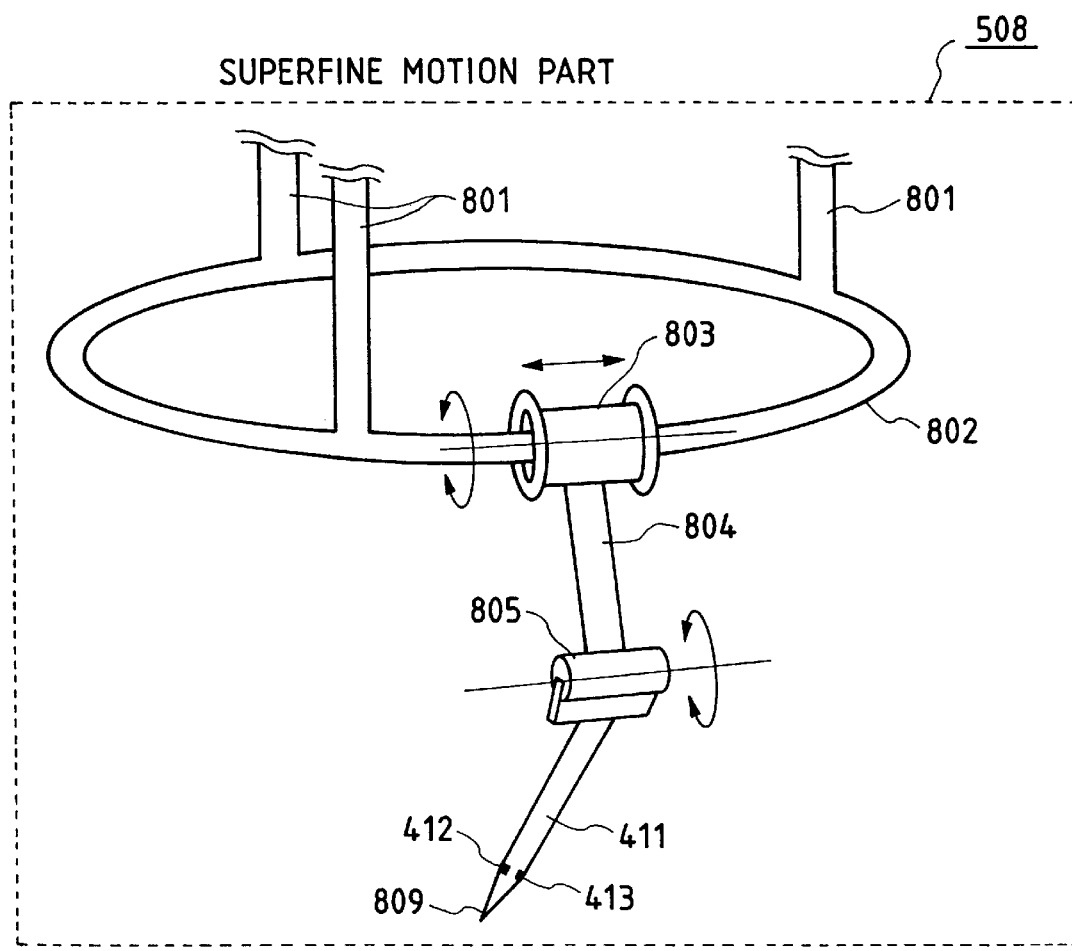
FIG. 8 is a schematic diagram showing a superfine motion part.
Figure 9:
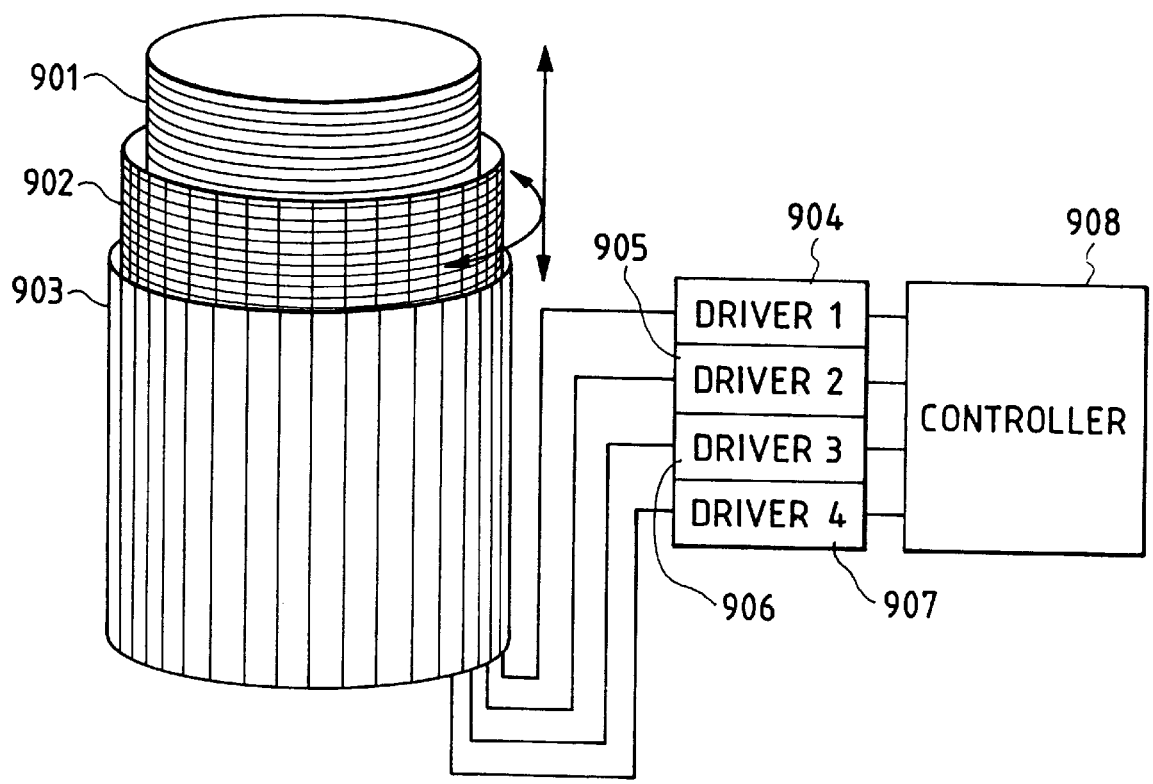
FIG. 9 is a schematic diagram showing a first joint of the superfine motion part.

FIG. 9 shows details of the first joint 803 in FIG. 8. The first joint 803 comprises an inner stator 901, i.e., a small portion of the ring rail 802, a multi-degree of freedom mover 902, an outer stator 903 to which the first link 804 is coupled securely, a driving circuit 904 for controlling an electrode voltage of the outer stator 903, driving circuits 905 and 907 for controlling electrode voltages of the peripheral surface and of the inner peripheral surface of the multi-degree of freedom mover 902, a driving circuit 906 for controlling an electrode voltage of the inner stator 901 and a main controller 908. Materials of the mover and stator are polyimide and adhesive. A conductive polymer compound mainly composed of carbon molecules is used as the electrode.

Ring-shaped electrodes are disposed on the periphery of the inner stator 901 and spaced vertically with respect to the axis of the cylinder. Electrodes are also disposed on the inner periphery of the multi-degree of freedom mover 902 in parallel with the inner stator 901 and a large number of linear electrodes are disposed on the periphery thereof vertically with respect to the inner stator 901. Although not shown, flanges are attached on the both sides of the multi-degree of freedom mover 902 to constrain the degree of freedom of the outer stator 903 only to rotation around the center line of the cylinder. A large number of linear electrodes are disposed on the inner periphery of the outer stator 903 in parallel with the electrodes on the periphery of the multi-degree of freedom mover 902.

Figure 10:
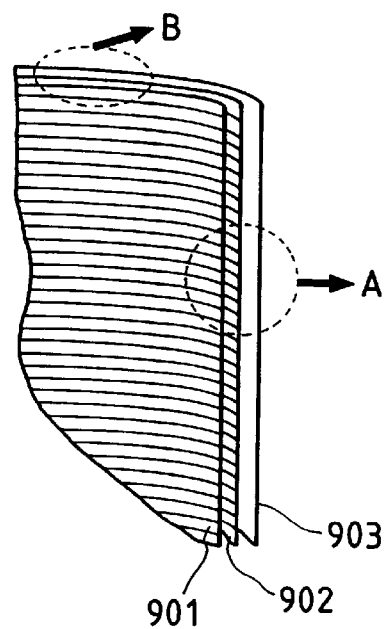
FIG. 10 is a section view of two parts of the first joint.
Figure 11:
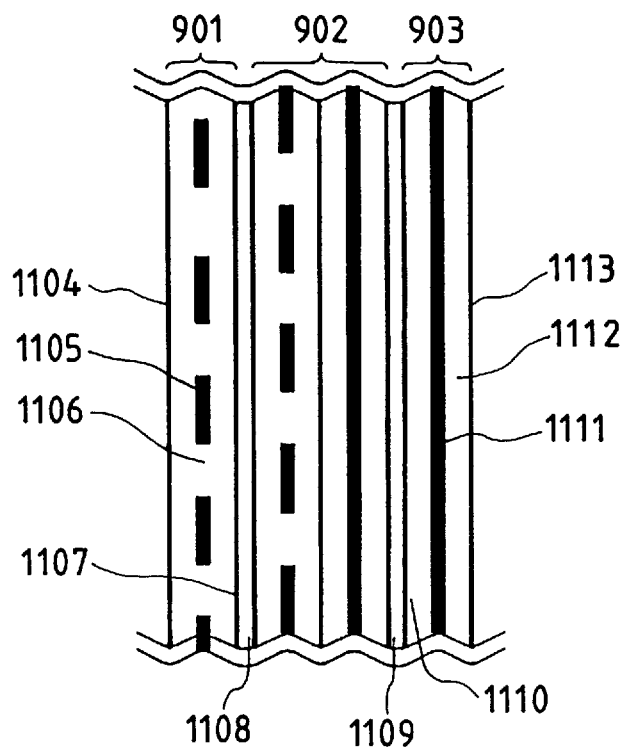
FIG. 11 is an enlarged view of the section at part A in FIG. 10.

FIG. 10 is a section view of the first joint 803, shown in FIG. 9, cut along a plane including the center axis and a plane orthogonal to that. FIG. 11 is an enlarged view of the section at part A in FIG. 10 and FIG. 12 is an enlarged view of the section at part B.

In FIG. 11, the outer stator 903 is covered with an inner cover 1110 and an outer cover film 1113 on both sides thereof and an adhesive 1112 is filled in between both films. Carbon polymer compound electrodes 1111 are disposed at equal intervals so that they extend along a line of intersection of the cylinder and plane including the center axis of the cylinder. Its section is like a chain line as shown in FIG. 12.

The structure of the peripheral portion of the multi-degree of freedom mover 902 is the same as that of the outer stator 903 and the structure of the inner peripheral portion thereof is the same as that of the inner stator 901. Insulating fluids 1108 and 1109 are filled between the inner stator 901 and the multi-degree of freedom mover 902 and between the multi-degree of freedom mover 902 and the outer stator 903, respectively.

Figure 12:
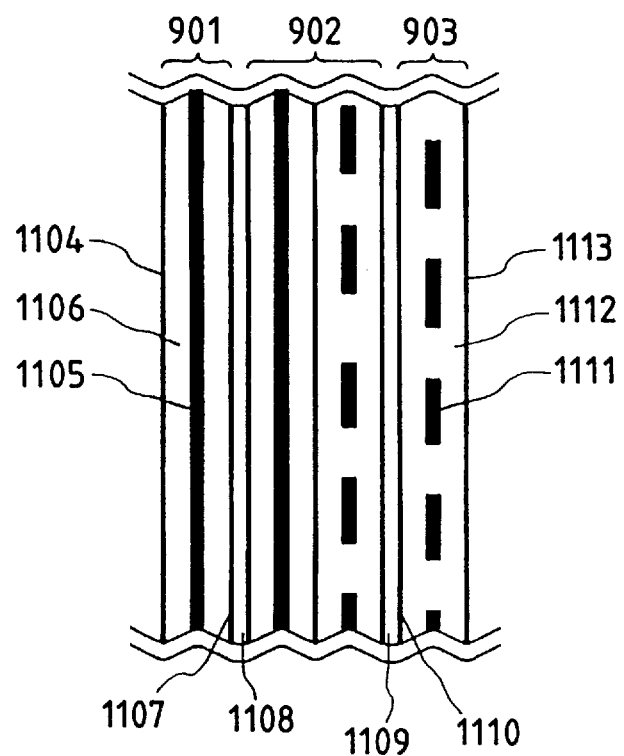
FIG. 12 is an enlarged view of the section at part B in FIG. 10.

FIG. 12 is an enlarged section view of part B in FIG. 10 and the same members are denoted with the same reference numerals. In this section view, the direction of the electrodes is opposite from that in FIG. 11 because the direction of the section is orthogonal to that in FIG. 11.

Figure 13:
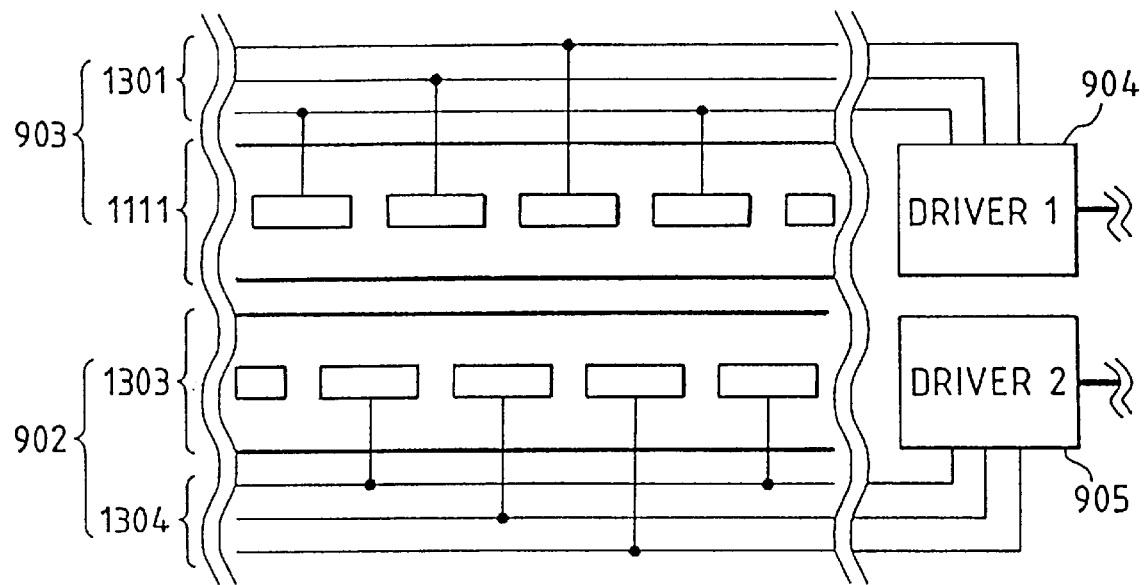
FIG. 13 is a schematic diagram showing a basic drive theory of the first joint.

Next, the basic operating principle of the first joint 803 will be explained with reference to FIG. 13. FIG. 13 is a section view showing a combination of the outer stator 903 and the peripheral portion of the multi-degree of freedom mover 902. Three-phase alternating voltages are applied to the electrode 1111 of the outer stator 903 and a peripheral electrode 1303 of the multi-degree of freedom mover 902, in a set of three electrodes, via wires 1301 and 1304. When the voltages applied to the electrodes 1111 and 1303 are antiphase or when their frequency is different, a driving force is generated between the mover and the stator, translating the mover 902 in the direction of axis of the cylinder. The same applies also between the inner portion of the multi-degree of freedom mover 902 and the inner stator 901.

Further, because the set of the electrodes at the inner portion is orthogonal to the set of the electrodes at the outer portion, the set of the inner electrodes generates, microscopically, a driving force in the tangential direction of a circular section vertical to the axis of the cylinder. Integrating this driving force in the circumferential direction turns it to a turning force around the axis and the multi-degree of freedom mover 902 rotates.

Further, the above-mentioned motions in the two directions are orthogonal from each other and one motion generated by one combination will not change the positional relationship of the electrodes in another combination. Accordingly, the first joint 803 can translate in the axial direction of the cylinder and rotate around the axis at the same time.

An explanation of the second joint 805 is omitted here because its structure is the same as the combination of the multi-degree of freedom mover 902 and the outer stator 903 in FIG. 9.

Figure 40:
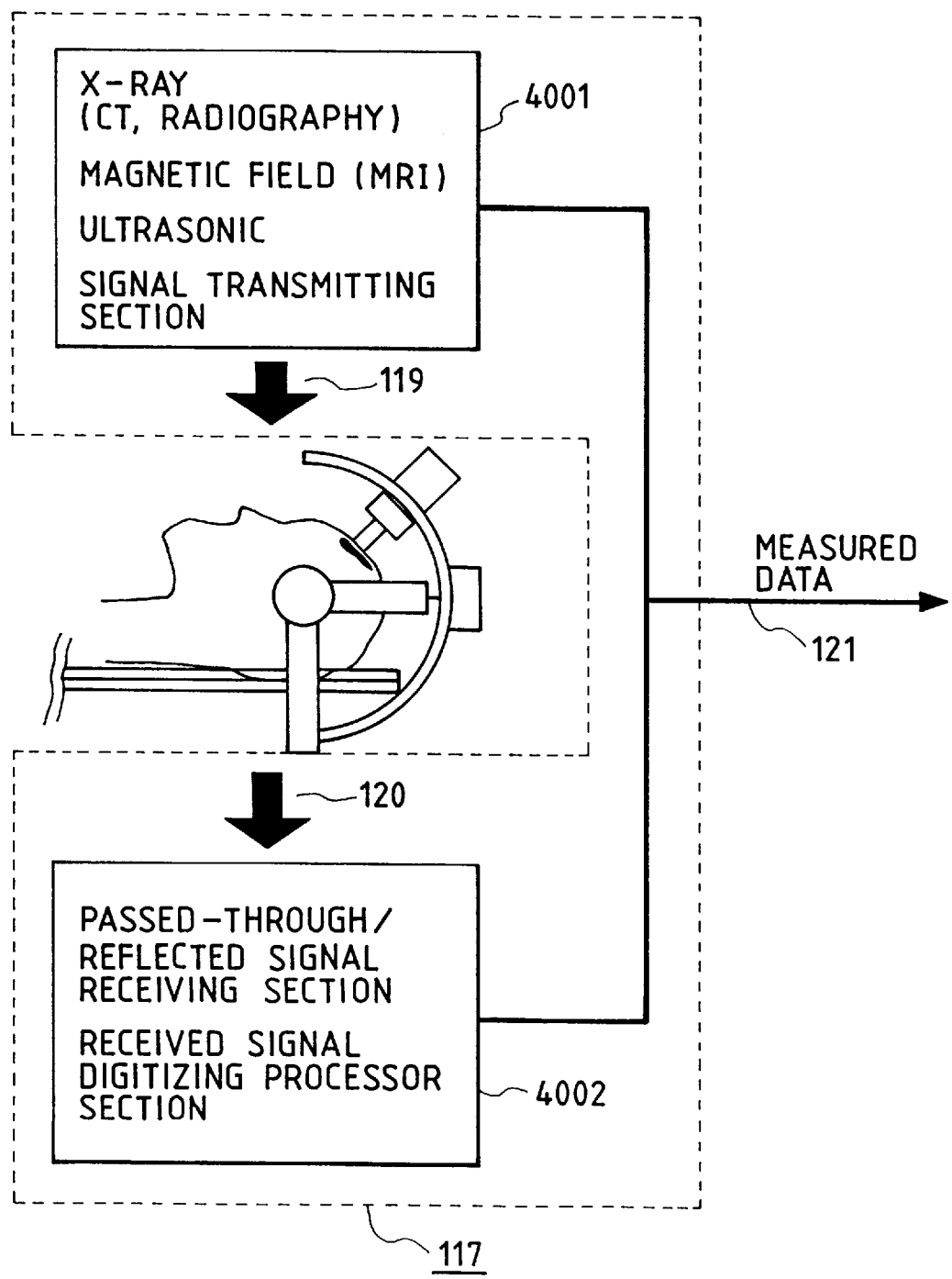
FIG. 40 is a block diagram showing in vivo data measuring means.

The in vivo data measuring means 117 will be explained below with reference to FIG. 40. The in vivo data measuring means 117 comprises a measurement signal transmitting section 4001 and a measurement signal receiving section 4002.

The measurement signal transmitting section 4001 is equipped with an X-ray tube, a superconductive magnet and magnetic coils, an ultrasonic transducer and the like so as to be able to transmit measurement signals in various modalities, such as X-ray, magnetic field and ultrasonic.

On the other hand, the measurement signal receiving section 4002 is equipped with receiving devices which correspond to each modality to receive an input signal 119 which penetrates through or is reflected by the body of the patient and comes out as an output signal 120.

An X-ray which has been transmitted from the X-ray tube and has penetrated through the body is received by an array of two-dimensional X-ray sensors. Signals which originate a 3-D CT image may be obtained in a very short time by turning those transmitting and receiving sections around the patient. This is a system called a cone-beam CT.

A fluctuating magnetic field generated by the magnetic coil is caught by a RF (Radio Frequency) probe. It adopts the same principle as a measuring instrument called a MRI. A transmitting section and a receiving section of the ultrasonic transducer is arranged and disposed in the shape of a two-dimensional array.

Thereby, the X-ray CT provides signals which originate the data as to the shape of the neighborhood of the patient including the bone and the MRI provides signals which originate data as to shape, visualized data of a difference of tissues, which is undistinguishable by the naked eye and visualized data of a brain function. The ultrasonic wave provides signals which originate data as to shape and data which indicate local abnormal blood stream and dyskinesia.

The measurement by means of the multiplex modalities described above is carried out with a very short period regardless of whether it occurs before or during an operation, and the obtained signal data is digitized and pre-processed in the signal receiving section 4002. The digitized measurement data 121 is sent to the measurement data processing means 118.

Figure 41:
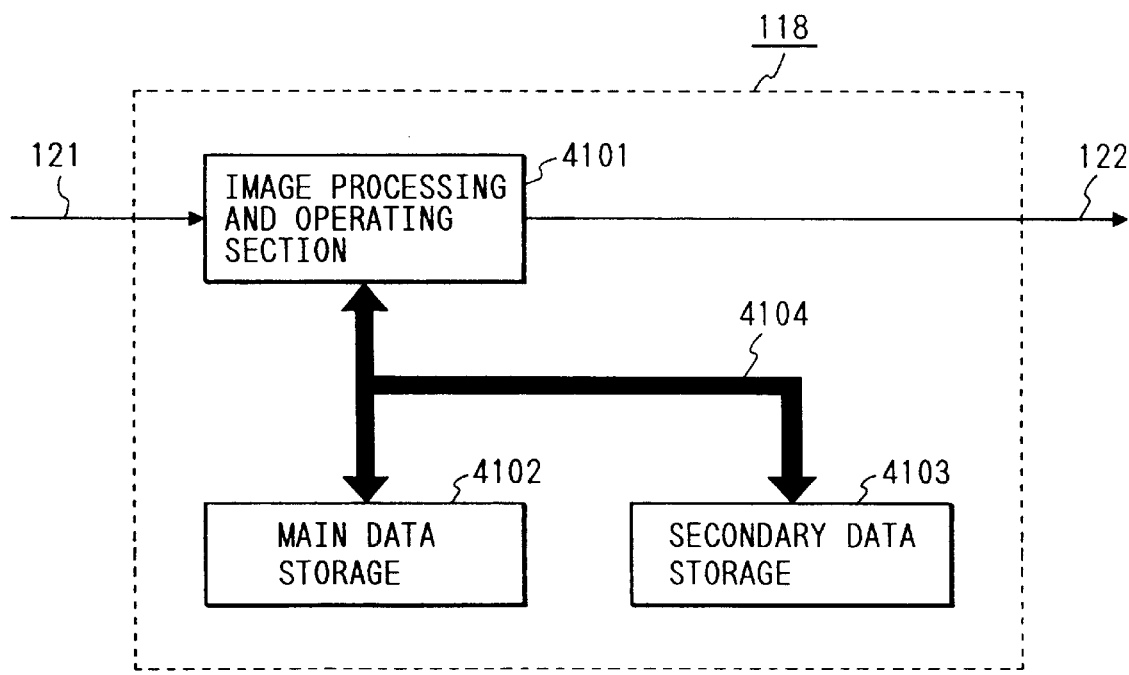
FIG. 41 is a block diagram showing measurement data processing means.

Next, the measurement data processing means 118 will be explained with reference to FIG. 41. The measurement data processing means 118 comprises an image processing and operating section 4101, a main storage 4102, a secondary data storage 4103 and an address and data bus 1104.

It is preferable to construct the image processing and operating section 4101 like a massively parallel computer. The main storage 4102 is a normal memory and the secondary data storage 4103 is a mass storage like an optical magnetic disk. These devices 4101 through 4103 are linked closely by the address and data bus 4101 to allow super-high speed image processing and operation.

The measured data 121 is stored in the main storage 4102 passing through the image processing and operating section 4101. It is processed and is reconstructed as three-dimensional image data by the image processing and operating section 4101. The reconstructed data 122 is sent to the realism control data generating means 101 to be synthesized with the other images.

By constructing the system as described above, the in vivo data is reconstructed in 3-D and visualized, regardless of whether the precessing occurs before or during the operation, and is presented to the surgical operator while being updated with a short period. The 3-D image data reconstructed at this time is stored in the secondary data storage 4103. This data is used in carrying out simulations and training, beside as well as during a surgical operation.

The explanation described above is applicable not only to the detail structure of the embodiment in FIG. 1 and of the support of a surgical operation, but also to training by way of simulation of surgery and for explanation of the surgical operation to the patient (informed consent).

The simulation training function will be explained below.

At first, a virtual diseased part is produced by the realism control data generating means 101. Actual diseased part image data, generated by reconstruction in 3-D from the measured data and stored in the secondary data storage 214 in FIG. 2 or the second storage 4103 in FIG. 41, is used or virtual diseased part image data is generated from some model. It is then displayed and virtual force reflection data 108 is generated and is sent to the manipulation command generating means 103. Because there is no force reflection from the actual world at this time, the virtual force reflection is equal to synthesized force reflection.

The virtual force reflection is calculated based on a dynamic model stored in the secondary data storage 214 within the work environment data processor 201. The calculation result is sent to the action command inputting means of each surgical operator to transfer the virtual force reflection.

The surgical operators manipulate the slave manipulators in the real world within the virtual environment. The manipulator moves following the intention of the surgical operator and detects each sensor data. Among them, only the visual sensor data is sent to the realism control data generating means 101 to combine with the virtual diseased part image data.

At this time, the simulation may be carried out by one person or the "bodily" training may be carried out by using the multi-to-one master/slave function described before. The secondary data storage 214 within the work environment data processor 201 records also each data time series of this simulation of surgery. Accordingly, the recorded result may be reproduced on another occasion to evaluate actions and decisions.

Next, the case when the surgical operation is explained to the patient will be described. Because the above-mentioned simulation result has been recorded, the contents of the operation may be explained by reproducing the result. Thereby, the patient can deepen his understanding of the operation and enhance his confidence in the surgical operator and the operation itself.

A case when the explanation is made by using actual, not virtual, operation record data is as follows. The data in the secondary data storage 214 within the work environment data processor 201 and the data in the secondary data storage 4103 in the measurement data processing means 118 contain data for synchronization. This data is combined and reproduced on the display 203 of the realism control data generating means 101 based on that data. It is possible to reproduce only the actual image or to reproduce only the measured data reconstructed into a 3-D image. The surgical operator can explain the operation to the patient having a similar symptom by reproducing the image.

Thereby, the patient can deepen his understanding of the operation and enhance his confidence in to the surgical operator and the surgerical operation itself similar to the case described above.

What is claimed is:

1. A remote surgery supporting system for supporting surgical operations of one or more surgical operators remote-controlling at least one of a surgical tool and a therapeutic instrument, comprising:

diseased tissue manipulating means carrying at least one of a surgical tool and therapeutic instrument;

in vivo data measuring means for measuring in vivo data by periodically applying one or more of fluctuating magnetic field, electromagnetic wave and ultrasonic wave to a diseased part of a patient and the surrounding part thereof before and during an operation and by measuring a penetrated or resonated signal;

measurement data processing means for generating a 3-D measured data image from the in vivo data measured by said in vivo data measuring means and providing an output indicative thereof;

work environment data detecting means for receiving information regarding the diseased part and for detecting an approaching state and a contact force which said diseased tissue manipulating means has applied to the diseased part and providing an output indicative thereof;

realism control data generating means for combining and processing the output of said working environment data detecting means and the output of said measurement data processing means to present to each surgical operator as realism control data;

action command inputting means for inputting actions taken by each surgical operator based on realism control data presented to each surgical operator by said realism control data generating means and providing an action command output; and manipulation command generating means for translating the action command output received from said action command inputting means to manipulation command data, for transmitting manipulation command data to said diseased tissue manipulating means and for transmitting a contact force detected by said working environment data detecting means to said diseased tissue manipulating means.

2. The remote surgery supporting system according to claim 1, wherein said diseased tissue manipulation means includes a mechanism for positioning said at least one of the surgical tool and therapeutic tool, said mechanism being made of a material and constructed so as to be less sensitive to a fluctuating magnetic field.

3. The remote surgery supporting system according to claim 1, wherein realism control data generated by said realism control data generating means contains at least one of:

a virtual image to be presented to a surgical operator by synthesizing the information received by said working environment data detecting means and a measured data image generated by said measurement data processing means;

a virtual sound field to be presented to the surgical operator as sound data; and virtual force reflection data to be presented to the surgical operator in combination with a contact force transmitted by said manipulation command generating means.

4. The remote surgery supporting system according to claim 3, wherein said realism control data contains said virtual image, and said virtual image is an image which represents stress at the diseased part and at the surrounding part thereof when the surgical tool or therapeutic instrument is in contact with the diseased part by using at least one of type, lightness and saturation of color.

5. The remote surgery supporting system according to claim 3, wherein said realism control data contains said virtual image, and said virtual image is an image which represents a distance between the surgical tool or therapeutic instrument and the diseased part when the surgical tool or therapeutic instrument is not in contact with the diseased part by using at least one of type, lightness and saturation of color.

6. The remote surgery supporting system according to claim 3, wherein said realism control data contains said virtual image, and said virtual image is an image which represents a positional deviation from a target, velocity and acceleration of the tip of a surgical tool or therapeutic instrument by using at least one of type, lightness and saturation of color.

7. The remote surgery supporting system according to claim 3, wherein said realism control data contains said virtual image, and said virtual image is a vector diagram indicating the moving direction of a tip of a surgical tool or therapeutic instrument.

8. The remote surgery supporting system according to claim 3, wherein said realism control data contains said virtual image, and said virtual image is an image produced by wavelength-converting an image in the neighborhood of the diseased part in an infrared range into that of a wavelength in a visible range.

9. The remote surgery supporting system according to claim 3, wherein said realism control data contains said virtual sound field, and said virtual sound field represents stress at a diseased part and at the surrounding part thereof when the surgical tool or therapeutic instrument is in contact with the diseased part using at least one of sound volume, timbre, musical interval and tone color.

10. The remote surgery supporting system according to claim 3, wherein said realism control data contains said virtual sound field, and said virtual sound filed represents the distance between a surgical tool or therapeutic instrument and a diseased part when the surgical tool or therapeutic instrument is not in contact with the diseased part using at least one of sound volume, timbre, musical interval and tone color.

11. The remote surgery supporting system according to claim 3, wherein said realism control data contains said virtual sound field, and said virtual sound field represents a positional deviation from a target, velocity and acceleration of a tip of the surgical tool or therapeutic instrument using at least one of sound volume, timbre, musical interval and tone color.

12. The remote surgery supporting system according to claim 3, wherein said realism control data contains said virtual sound field, and said virtual sound field represents a magnitude and direction of a vector, which indicates a moving direction of the surgical tool or therapeutic instrument, using at least one of sound volume, timbre, musical interval and tone color of wind-cutting sound.

13. The remote surgery supporting system according to claim 3, wherein said realism control data contains said virtual sound field, and said virtual sound field represents a temperature, in the neighborhood of a diseased part obtained from an infrared image, using at least one of sound volume, timbre, musical interval and tone color.

14. The remote surgery supporting system according to claim 3, wherein said realism control data contains said virtual force reflection, and said virtual force reflection is calculated from at least one-order of differential values relating to a distance between a position of a tip of a surgical tool or therapeutic instrument and the diseased part and a timing thereof.

15. The remote surgery supporting system according to claim 3, wherein said realism control data contains said virtual force reflection, and said virtual force reflection represents a distribution of intensity of an infrared image in the neighborhood of a diseased part by force exerted in the opposite direction from the depth of the diseased part.

16. The remote surgery supporting system according to claim 1, wherein said working environment data detecting means detects force sensor data, said realism control data generating means generates a virtual force reflection to each surgical operator via said action command inputting means, said manipulation command generating means transmits a synthesized force reflection obtained by combining said force sensor data detected by said working environment data detecting means and said virtual force reflection generated by said realism control data generating means.

17. The remote surgery supporting system according to claim 16, wherein said manipulation command generating means includes manipulation force computing means for calculating a force applied to said diseased tissue manipulating means in response to other surgical operators inputting action commands via said action command inputting means and means for outputting a weighted result representing a sum of a force caused by a manipulation of each surgical operator calculated by said manipulation force computing means and said synthesized force reflection.

18. The remote surgery supporting system according to claim 1, wherein said diseased tissue manipulating means positions said at least one of the surgical tool and therapeutic instrument against the diseased part as it receives a manipulation command as an input and said at least one of the surgical tool and therapeutic instrument causes deformation, destruction or degeneration of diseased tissues by providing at least one of kinetic energy, light energy, electrical energy and thermal energy.

19. The remote surgery supporting system according to claim 18, further comprising a source of said kinetic energy being a manipulator having a plurality of degrees of freedom and a source of said light energy and thermal energy being a laser beam generator which transmits the laser beam through optical fibers.

20. The remote surgery supporting system according to claim 19, wherein a driving mechanism is provided for said manipulators, said driving mechanism being an actuator utilizing electrostatic force acting between a plurality of electrodes.

21. The remote surgery supporting system according to claim 20, wherein said actuator includes a non-magnetic organic material.

22. The remote surgery supporting system according to claim 19, wherein said manipulator includes a non-magnetic material.

23. The remote surgery supporting system according to claim 1, wherein said at least one of the surgical tool and therapeutic instrument includes a Peltier effect element.

24. The remote surgery supporting system according to claim 1, further comprising storage means for storing at least one of the realism control data generated by said realism control data generating means and the measured data image generated by said measurement data processing means.

25. The remote surgery supporting system according to claim 24, further comprising models for generating at least one of said realism control data and said measured data image being stored in said storage means.

26. The remote surgery supporting system according to claim 1, wherein the information regarding the diseased part received by the work environment data detecting means includes at least the output from the measurement data processing means.

27. A remote surgery supporting system for supporting at least one surgical operation of at least one surgical operator remote-controlling at least one of a surgical tool and a therapeutic instrument, comprising:

means for carrying at least one of a surgical tool and therapeutic instrument, said at least one of the surgical tool and the therapeutic instrument including an end effector for causing at least one of deformation, destruction and degeneration of diseased tissues of a diseased part of a patient by at least one of generating and transmitting at least one of kinetic energy, light energy, electric energy and thermal energy thereto;

a driving mechanism for enabling movement of said at least one of the surgical tool and the therapeutic instrument;

means for calculating at least one virtual force reflection in accordance with a location and movement of said at least one of the surgical tool and the therapeutic instrument with respect to the diseased part and providing an output indicative thereof;

a master manipulator for outputting an action command in response to an input from each surgical operator;

manipulation command generating means for translating at least one of an action command output from said master manipulator and the output from the means for calculating into a manipulation command output; and a slave manipulator for positioning said at leas tone of the surgical tool and the therapeutic instrument against the diseased part using said driving mechanism by interpreting the manipulation command output from said manipulation command generating means.

28. The remote surgery supporting system according to claim 27, wherein said means for calculating calculates the at least one virtual force reflection from at least one differential value related to a distance between a position of a tip of said at least one of the surgical tool and the therapeutic instrument and the diseased part with respect to time.

29. The remote surgery supporting system according to claim 27 or 28, further comprising:

in vivo data measuring means for measuring in vivo data by applying at least one of a fluctuating magnetic field, an electromagnetic wave and ultrasonic wave to the diseased part and the surrounding part thereof before and during an operation and by measuring a penetrated or resonated signal;

measurement data processing means for generating a 3-D measured data image from the in vivo data measured by said in vivo data measuring means and providing an output indicative thereof;

work environment data detecting means for receiving information regarding the diseased part and for detecting an approaching state and a contact force which said carrying means has applied to the diseased part and providing an output indicative thereof; and control data generating means including said calculating means for combining and processing the output of said working environment data detecting means and the output of said measurement data processing means to present the generated control data to each surgical operator.

30. The remote surgery supporting system according to claim 29, wherein the generated control data generated by said control data generating means contains at least one of:

a virtual image to be presented to a surgical operator by synthesizing image data taken in by said working environment data detecting means and a measured data image generated by said measurement data processing means;

a virtual sound field to be presented to the surgical operator as sound data; and virtual force reflection data to be presented to the surgical operator in combination with a contact force transmitted by said manipulation command generating means.

31. The remote surgery supporting system according to claim 27, further comprising means for providing the output of said means for calculating to a respective surgical operator.

32. A remote surgery supporting method for supporting at least one of a plurality of surgical operators performing surgical procedures on a diseased part of a patient by driving a slave manipulator equipped with at least one of a surgical tool and therapeutic instrument by a respective one of the at least one of the plurality of surgical operators manipulating a respective master manipulator, comprising a step of driving one slave manipulator using a combined command, said combined command being obtained by the substeps of multiplying action commands output from the master manipulator of the respective one of the at least one of the plurality of surgical operators with a weighting factor to produce weighted action commands and adding the weighted action commands.

33. The remote surgery supporting method according to claim 32, comprising steps of:

measuring in vivo data of the diseased part to produce measured data and generating measured image data from said measured data;

taking an image of the diseased part or said at least one of the surgical tool and the therapeutic instrument to generate diseased part image data; and combining the measured image data and diseased part image data to present an image to the respective one of the at least one of the plurality of surgical operators.

34. The remote surgery supporting method according to claim 32, comprising a step of detecting a distance or contact force between said at least one of the surgical tool and therapeutic instrument and the diseased part to generate data to present to the respective ones of the at least one of the plurality of surgical operators.

35. The remote surgery supporting method according to claim 32, comprising a step of measuring a distribution of temperature of the diseased part to generate data to present to the at least one of the plurality of the surgical operators.

36. The remote surgery supporting method according to claim 32, comprising a step of determining a moving velocity, an acceleration and a deviation from a target position of a tip of said at least one of the surgical tool and therapeutic instrument to generate data to present to the respective ones of the at least one of the surgical operators.

37. The remote surgery supporting method according to claim 32, comprising a step of combining a force reflection of said at least one of the surgical tool and therapeutic instrument and a manipulation force produced by the respective ones of the at least one of the plurality of surgical operators to transmit to said master manipulator corresponding to a respective one of the at least one of the plurality of surgical operators.

38. A remote surgery supporting method for supporting surgical operations of at least one surgical operator remote-controlling diseased tissue manipulating means including at least one of a surgical tool and a therapeutic instrument, comprising the steps of:

manipulating diseased tissue by diseased tissue manipulating means carrying the at least one of the surgical tool and the therapeutic instrument;

measuring in vivo data by periodically applying at least one of a fluctuating magnetic field, electromagnetic wave and ultrasonic wave to a diseased part of a patient and a surrounding part thereof before and during an operation and by measuring at least one of a penetrated and resonated signal;

processing the measured in vivo data for generating a 3-D measured data image;

detecting work environment data including taking an image data of the diseased part and detecting an approaching state and a contact force of the diseased tissue manipulating means with the diseased part;

generating realism control data by combining and processing the detected working environment data and the processed measured in vivo data to present realism control data to a respective surgical operator;

inputting actions taken by a respective surgical operator based on the realism control data presented to a respective surgical operator and outputting action commands; and generating manipulation commands by translating an outputted action command to manipulation command data, and transmitting the manipulation command data and the detected contact force to the diseased tissue manipulating means.

39. A remote surgery supporting method for supporting at least one surgical operation of at least one surgical operator remote-controlling at least one of a surgical tool and a therapeutic instrument, comprising the steps of:

carrying the at least one of the surgical tool and the therapeutic instrument, the at least one of the surgical tool and the therapeutic instrument including an end effector for causing at least one of deformation, destruction and degeneration of diseased tissues of a diseased part of a patient by at least one of generating and transmitting at least one of kinetic energy, light energy, electric energy and thermal energy thereto;

moving the at least one of the surgical tool and the therapeutic instrument by a driving mechanism;

calculating at least one virtual force reflection in accordance with a location and movement of said at least one of the surgical tool and the therapeutic instrument with respect to the diseased part and providing an output indicative thereof;

outputting an action command by a master in response to an input from each surgical operator;

generating a manipulation command by translating at least one of an action command output from the master manipulator and the virtual force into a manipulation command output; and positioning the at least one of the surgical tool and the therapeutic instrument against the diseased part by a slave manipulator using the driving mechanism by interpreting the manipulation command output from the manipulation command generating means.

40. The remote surgery supporting method according to claim 39, further comprising the step of presenting the calculated at least one virtual force reflection to a respective surgical operator.

* * * * *